United States Patent
Vaganay et al.

(10) Patent No.: US 10,508,968 B1
(45) Date of Patent: Dec. 17, 2019

(54) SYSTEMS, METHODS AND APPARATUS FOR IN-SERVICE TANK INSPECTIONS

(71) Applicant: SQUARE ROBOT, INC., Boston, MA (US)

(72) Inventors: Jerome Vaganay, Norwell, MA (US);
Eric Levitt, Lincolnville, ME (US);
William O'Halloran, Boston, MA (US)

(73) Assignee: Square Robot, Inc., Boston, MA (US)

( * ) Notice: Subject to any disclaimer, the term of this patent is extended or adjusted under 35 U.S.C. 154(b) by 0 days.

(21) Appl. No.: 16/534,009

(22) Filed: Aug. 7, 2019

Related U.S. Application Data

(63) Continuation of application No. 16/526,412, filed on Jul. 30, 2019.

(60) Provisional application No. 62/796,533, filed on Jan. 24, 2019, provisional application No. 62/855,518, filed on May 31, 2019.

(51) Int. Cl.
| | | |
|---|---|---|
| *G01M 3/32* | (2006.01) | |
| *B65D 90/50* | (2019.01) | |
| *B65D 88/12* | (2006.01) | |
| *G01M 3/24* | (2006.01) | |

(52) U.S. Cl.
CPC ......... *G01M 3/3236* (2013.01); *B65D 88/128* (2013.01); *B65D 90/50* (2013.01); *G01M 3/24* (2013.01)

(58) Field of Classification Search
CPC .... G01M 3/3236; G01M 3/24; B65D 88/128; B65D 90/50
See application file for complete search history.

(56) References Cited

U.S. PATENT DOCUMENTS

| | | | | |
|---|---|---|---|---|
| 5,942,687 A | * | 8/1999 | Simmonds | G01B 17/02 73/579 |
| 6,104,970 A | * | 8/2000 | Schmidt, Jr. | B62D 55/32 701/2 |
| 10,012,561 B2 | * | 7/2018 | Walker | G01M 3/24 |

FOREIGN PATENT DOCUMENTS

| | | |
|---|---|---|
| CN | 101659053 B | 4/2011 |
| CN | 104698074 A | 6/2015 |
| CN | 103261920 B | 11/2016 |
| CN | 104564023 B | 11/2017 |
| CN | 106904258 B | 3/2019 |

(Continued)

OTHER PUBLICATIONS

Bogue, Robert "Applications of Robotics in Test and Inspection" Industrial Robot: An International Journal, Jan. 2018, pp. 169-174 (6 pages).

*Primary Examiner* — David Z Huang
(74) *Attorney, Agent, or Firm* — Foley & Lardner LLP

(57) ABSTRACT

Systems, methods and apparatuses for inspecting a tank containing a flammable fluid are provided. A vehicle configured to inspect the tank can include a propeller, a battery, a control unit, an inspection device, and a ranging device. The battery provides power to the propeller, the control unit, the inspection device, and the ranging device. The control unit generates a map of the tank. The control unit determines a first position of the vehicle on the map of the tank. The propeller moves the vehicle through the flammable fluid in the tank. The inspection device determines a quality metric of a portion of the tank. The control unit causes the propeller to move the vehicle from the first position to a second position within the tank. The control unit determines the quality metric for the portion of the tank at the second position within the tank, and stores the quality metric.

20 Claims, 10 Drawing Sheets

(56) References Cited

FOREIGN PATENT DOCUMENTS

| KR | 20140037475 A | | 3/2014 | |
|---|---|---|---|---|
| RU | 2009146620 A | | 6/2011 | |
| WO | WO-2016/075864 A1 | | 5/2016 | |
| WO | WO-2018/104780 A2 | | 6/2018 | |
| WO | WO-2019035856 A1 | * | 2/2019 | ........... G01N 29/225 |

* cited by examiner

SYSTEMS, METHODS AND APPARATUS FOR IN-SERVICE TANK INSPECTIONS

CROSS-REFERENCES TO RELATED APPLICATIONS

This application claims the benefit of priority under 35 U.S.C. § 120 as a continuation of U.S. patent application Ser. No. 16/526,412, filed Jul. 30, 2019, which claims the benefit of priority under 35 U.S.C. § 119 to U.S. Provisional Patent Application No. 62/855,518, filed May 31, 2019, and claims the benefit of priority under 35 U.S.C. § 119 to U.S. Provisional Patent Application No. 62/796,533, filed Jan. 24, 2019, each of which is hereby incorporated by reference herein in its entirety.

BACKGROUND

Tanks can store fluids or liquids, including flammable fluids such as oil or gas. The fluid can corrode portions of the tank that come into contact with the fluid. External surfaces of the tank can corrode due to water or other fluids under the floor of the tank, or water that leaked into the tank through, for example, a roof seal and sank below the hydrocarbon fluid due to its higher density. Corrosive elements in the hydrocarbon fluid can also contribute to corrosion. This corrosion can eventually cause the tank to leak. However, it can be challenging to determine the integrity of the tank to prevent leaks.

SUMMARY

This disclosure is directed to systems, methods and apparatus of inspecting a tank containing a flammable fluid. Due to the technical challenges of inspecting a tank containing a flammable fluid, tanks inspections may be performed on empty tanks that are out-of-service. However, out-of-service inspection entails many hazardous steps. For example, the tank is first emptied of its liquid content. A large opening is then cut in the side of the tank to allow people and tools to enter. The residual sediments on the floor are collected, removed from the tank and safely disposed of The atmosphere inside the tank is degassed and rendered safe. Human operators then enter the confined space under harsh and hazardous conditions to perform tedious plate-by-plate floor inspection. Once the inspection is complete, plates are welded to close the opening on the side of the tank, and the tank refilled with flammable fluid. These additional steps taken to inspect a tank can be time consuming, resource intensive, or hazardous.

Systems, methods and apparatus of this technical solution provide an autonomous vehicle that can inspect a tank containing a flammable fluid. The autonomous vehicle of this technical solution can perform an in-service tank inspection. An in-service tank inspection can refer to inspecting the tank while the flammable fluid is still contained in the tank. In some cases, an in-service tank inspection can refer to a closed tank inspection, such as inspecting a tank containing a flammable fluid while the lid of the tank is closed or sealed. To perform an in-service tank inspection, the autonomous vehicle of this technical solution can be tetherless and include a propeller, battery, and control unit that can automatically perform a tank inspection process. By automatically performing an in-service tank inspection with the tank lid closed, the autonomous vehicle can save time, reduce resource utilization and increase safety by inspecting the tank without having to empty the tank, which can allow for more frequent tank inspections. The system can more accurately predict the quality, integrity or state of the tank by performing more frequent tank inspection, or collecting inspection data at different intervals.

At least one aspect is directed to a vehicle to inspect a tank containing a flammable fluid. The vehicle can include a propeller, a battery, a control unit, an inspection device, and a ranging device. The battery can provide power to the propeller, the control unit, the inspection device, and the ranging device. The control unit can generate a map of the tank based on data received from the ranging device. The ranging device can include an acoustic sensor or electromagnetic radiation sensor capable of providing a measurement of the distance between the robot and the environment (e.g., tank shell and obstacles such as pipes or roof support columns). The control unit can determine a first position of the vehicle on the map of the tank. The propeller, which can be electrically connected to the battery, can move the vehicle through the flammable fluid in the tank. The inspection device, which can be electrically connected to the battery, can determine a quality metric of a portion of the tank. The control unit can be electrically connected to the battery, the ranging device, the propeller and the inspection device. The control unit can cause the propeller to move the vehicle from the first position to a second position within the tank. The control unit can determine, via the inspection device, the quality metric for the portion of the tank at the second position within the tank. The control unit can store, in a data structure in memory of the vehicle, the quality metric corresponding to the second position within the tank.

The control unit of the vehicle can execute a diagnostic program prior to causing the propeller to move the vehicle. The control unit of the vehicle can be configured to determine, based on results of a diagnostic program, to initiate a tank inspection process, and provide, based on the tank inspection process, a command to cause the propeller to move the vehicle from the first position to the second position within the tank. The control unit of the vehicle can be configured to disable, based on a diagnostic program, the propeller to prevent the propeller from moving the vehicle from the second position. The control unit of the vehicle can be further configured to execute a diagnostic program prior to causing the propeller to move the vehicle, and set a speed of the propeller based on a result of the diagnostic program.

The control unit of the vehicle can further be configured to cause the propeller to move the vehicle to a plurality of portions of the tank, generate a map of the tank based on traversing a plurality of portions of the tank, and detect an exit condition based on the generated map. The control unit of the vehicle can be further configured to adjust a speed of the propeller based on a current location of the vehicle on the map and detect the exit condition based on an amount of power available in the battery. A plurality of propellers of the vehicle can be configured to move the vehicle in one or more directions. The propeller of the vehicle can be one of a controllable-pitch propeller, skewback propeller, modular propeller, or Voith Schneider propeller. The quality metric of the vehicle can indicate a thickness of the portion of the tank at the second position within the tank.

At least one aspect is directed to a method of inspecting a tank containing a flammable fluid. The method can be performed by a vehicle having one or more processors and memory. The method can include lowering, via a cable, the vehicle into the tank containing the flammable fluid, wherein the vehicle can comprise a propeller, a battery, a control unit, an inspection device, and a ranging device. The method can include removing, subsequent to deploying the vehicle, the cable from the tank. The method can include moving, by the propeller, the vehicle through the flammable fluid in the tank. The method can include generating, by the control unit based on data received from the ranging device, a map of the tank. The method can include determining, by the control unit, a first position of the vehicle on the map of the tank. The method can include causing, by the control unit of the vehicle, the propeller to move from the first position to a second position within the tank. The method can include determining, via the inspection device, a quality metric for a portion of the tank corresponding to the second position on the map. The method can include storing, in a data structure in memory of the vehicle, the quality metric corresponding to the second position within the tank.

The method can include executing, by the control unit, a diagnostic program prior to causing the propeller to move the vehicle. The method can include determining, by the control unit based on results of a diagnostic program, to initiate a tank inspection process, and providing, by the control unit based on the tank inspection process, a command to cause the propeller to move the vehicle from the first position to the second position within the tank. The method can include disabling, by the control unit based on a diagnostic program, the propeller to prevent the propeller from moving the vehicle from the second position. The method can include executing, by the control unit, a diagnostic program prior to causing the propeller to move the vehicle, and setting, by the control unit, a speed of the propeller based on a result of the diagnostic program.

The method can include causing, by the control unit, the propeller to move the vehicle to a plurality of portions of the tank, generating, by the control unit, a map of the tank based on traversing a plurality of portions of the tank, and detecting, by the control unit, an exit condition based on the generated map. The method can include adjusting, by the control unit, a speed of the propeller based on a current location of the vehicle on the map. The method can include detecting, by the control unit, the exit condition based on an amount of power available in the battery. The method can include moving, by a plurality of propellers, the vehicle in one or more directions. The propeller of the method can be one of a controllable-pitch propeller, skewback propeller, modular propeller, or Voith Schneider propeller. The quality metric of the method can indicate a thickness of the portion of the tank at the second position within the tank.

At least one aspect is directed to a system to inspect a tank containing a flammable fluid. The system can include a battery, a control unit, an inspection device having one or more conductors, and a ranging device. The inspection device can be electrically connected to the control unit and the battery. The inspection device can receive, from the control unit responsive to identifying a first position of the vehicle on a map of the tank based on data from the ranging device, a command to initiate inspection at the first position on the map. The inspection device can change, responsive to the command to initiate inspection, a magnetic field in the one or more conductors to induce loops of electric current that extend towards a portion of the tank corresponding to the first position on the map. The inspection device can detect values corresponding to the induced loops of electric current at the portion of the tank corresponding to the first position on the map. The inspection device can provide, to the control unit, data comprising the detected values to cause the control unit to determine a quality metric at the portion of the tank corresponding to the first position of the vehicle on the map, and store, in memory of the vehicle, the quality metric.

The inspection device can generate pulsed eddy currents to determine the quality metric. The inspection device can include a plurality of conductors arranged in an array to generate array eddy currents to determine the quality metric at a portion of the tank corresponding to a second position of the vehicle on the map. The inspection device can include an ultrasonic array or ultrasonic phased array system to determine a second quality metric at the portion of the tank corresponding to the first position of the vehicle on the map.

The inspection device can include at least two different types of sensors. The inspection device can obtain measurements from the at least two different types of sensors to generate the quality metric at the portion of the tank corresponding to the first position of the vehicle on the map. The quality metric can indicate a thickness of the portion of the tank corresponding to the first position of the vehicle on the map. The quality metric can indicate a predictive corrosion metric based on a plurality of tank inspection performed by the vehicle during a time interval. The inspection device can selects, based on a condition associated with the portion of the tank corresponding to the first position of the vehicle on the map, one of the at least two different types of sensors to inspect the portion of the tank.

The system can include a model generator that generates a risk-based inspection model based on a time-series of quality metrics determined based on the loops of electric current provided by the inspection device that extend towards the portion of the tank. The model generator can aggregate historical quality metrics obtained from a plurality of tank inspections to forecast a level of thickness of the tank based on the quality metric.

The ranging device can detect acoustic waves reflected off one or more portions of the tank, and the control unit generates the map of the tank based on the detected acoustic waves.

At least one aspect is directed to a method of inspecting a tank containing a flammable fluid. The method can include lowering, via a cable, a vehicle into the tank containing the flammable fluid. The vehicle can include a battery, a control unit, an inspection device having one or more conductors, and a ranging device. The method can include removing, subsequent to deploying the vehicle, the cable from the tank. The method can include the inspection device receiving, from the control unit responsive to identifying a first position of the vehicle on a map of the tank based on data from the ranging device, a command to initiate inspection at the first position on the map. The method can include the inspection device charging, responsive to the command to initiate inspection, a magnetic field in the one or more conductors to induce loops of electric current that extend towards a portion of the tank corresponding to the first position on the map. The method can include the inspection device detecting values corresponding to the induced loops of electric current at the portion of the tank corresponding to the first position on the map. The method can include the inspection device providing, to the control unit, data comprising the detected values to cause the control unit to determine a quality metric at the portion of the tank corresponding to the first position of the vehicle on the map, and store, in memory of the vehicle, the quality metric.

The method can include the inspection device generating a pulsed eddy current. The method can include determining the quality metric based on the pulsed eddy current.

The method can include generating, by a plurality of conductors of the inspection device, array eddy currents. The method can include determining the quality metric at a portion of the tank corresponding to a second position of the vehicle on the map based on the array eddy currents.

The method can include determining, via an ultrasonic array or ultrasonic phased array system of the inspection device, a second quality metric at the portion of the tank corresponding to the first position of the vehicle on the map.

The method can include generating the quality metric at the portion of the tank corresponding to the first position of the vehicle on the map by obtaining measurements from at least two different types of sensors of the inspection device. The quality metric can indicate a thickness of the portion of the tank corresponding to the first position of the vehicle on the map. The quality metric can indicate a predictive corrosion metric based on a plurality of tank inspection performed by the vehicle during a time interval.

The method can include generating, by a model generator, a risk-based inspection model based on a time-series of quality metrics determined based on the loops of electric current provided by the inspection device that extend towards the portion of the tank. The method can include aggregating historical quality metrics obtained from a plurality of tank inspections. The method can include forecasting, using the aggregated historical quality metrics, a level of thickness of the tank based on the quality metric.

The method can include receiving acoustic waves reflected off one or more portions of the tank. The method can include generating the map of the tank based on the acoustic waves.

At least one aspect is directed to a vehicle to inspect a tank containing a flammable fluid. The vehicle can include a propeller, a latch mechanism, a pressure switch, and an inspection device. The vehicle can include a control unit in communication with the propeller, the latch mechanism, the pressure switch, and the inspection device. The control unit can receive an indication from the pressure switch to power on. The control unit can receive the indication responsive to the pressure switch detecting an ambient pressure greater than a minimum threshold. The control unit can receive, from the latch mechanism, an indication of a state of the latch mechanism. The control unit can determine, based on the state of the latch mechanism, that the cable used to lower the vehicle into the tank containing the flammable fluid is detached from the vehicle. The control unit can command, responsive to the determination that the cable is detached from the vehicle, the propeller to move the vehicle through the flammable fluid. The control unit can determine, via the inspection device and subsequent to generation of a portion of a map, a quality metric of a portion of the tank.

The pressure switch can detect that the vehicle is submerged by a threshold depth in the flammable fluid. The pressure switch can provide, responsive to detection of the threshold depth, an indication to power on the control unit of the vehicle. The vehicle can be powered off as it is lowered through a vapor layer in the tank above the flammable fluid.

The latch mechanism can disengage the cable used to lower the vehicle into the flammable fluid in the tank. The latch mechanism can couple the cable to the vehicle to lower the vehicle into the flammable fluid in the tank. The vehicle can include an actuator that locks or unlocks the latch mechanism. The control unit can cause the actuator to unlock the latch mechanism to disengage the cable subsequent to the vehicle lowered into the flammable fluid in the tank.

The control unit can detect an exit condition in a tank inspection process. The control unit can cause the latch mechanism to re-engage the cable to couple to the cable to the vehicle. The cable can be a passive rope, such as a passive metal rope.

The control unit can execute a diagnostic program to detect a state of the cable. The control unit can generate, based on the state of the cable, a command to control at least one of the propeller or the latch mechanism coupling the cable to the vehicle.

The sensor can determine that the vehicle is in contact with the floor of the tank. The control unit can detect, via the sensor, that the vehicle is in contact with the tank floor. The control unit can command the latch mechanism to decouple the cable from the vehicle in the flammable fluid. The control unit can command the propeller to move the vehicle responsive to the second state of the latch mechanism.

The control unit can receive, from a remote computing device, an indication that the cable is decoupled from the vehicle in the flammable fluid. The control unit can receive, from a remote computing device, an indication to perform a tank inspection process comprising causing the propeller to move the vehicle to one or more positions in the tank, and determine one or more quality metrics.

At least one aspect is directed to a method of inspecting a tank containing a flammable fluid. The method can include lowering, via a cable, a vehicle into the tank containing the flammable fluid. The vehicle can include a control unit, a propeller, a pressure switch, a latch mechanism, and an inspection device. The method can include the control unit receiving, from the pressure switch, an indication to power on. The method can include removing, subsequent to deploying the vehicle, the cable from the tank. The method can include the control unit receiving, from the latch mechanism, an indication of a state of the latch mechanism. The method can include the control unit determining, based on the state of the latch mechanism, that the cable used to lower the vehicle into the tank containing the flammable fluid is detached from the vehicle. The method can include the control unit commanding, responsive to the determination that the cable is detached from the vehicle, the propeller to move the vehicle through the flammable fluid. The method can include the control unit determining, via the inspection device and subsequent to generation of a portion of a map, a quality metric of a portion of the tank.

The method can include detecting, by the pressure switch, that the vehicle is submerged by a threshold depth in the flammable fluid. The method can include providing, by the pressure switch responsive to detection of the threshold depth, an indication to power on the control unit of the vehicle, wherein the vehicle is powered off as it is lowered through a vapor layer in the tank above the flammable fluid.

The method can include the latch mechanism disengaging the cable used to lower the vehicle into the flammable fluid in the tank. The method can include coupling, via the latch mechanism, the cable to the vehicle to lower the vehicle into the flammable fluid in the tank. The method can include locking or unlocking, by the control unit in communication with an actuator, the latch mechanism to disengage the cable subsequent to the vehicle lowered into the flammable fluid in the tank.

The method can include detecting, by the control unit, an exit condition in a tank inspection process. The method can include re-engaging, by the control unit, the latch mechanism with the cable to couple to the cable to the vehicle. The cable can be a passive rope, such as a passive metal rope.

The method can include executing, by the control unit, a diagnostic program to detect a state of the cable. The method can include generating, by the control unit based on the state of the cable, a command to control at least one of the propeller or the latch mechanism coupling the cable to the vehicle.

The method can include determining, via a sensor, that the vehicle is in contact with the floor of the tank. The method can include commanding, by the control unit, the latch mechanism to decouple the cable from the vehicle in the flammable fluid. The method can include commanding, by the control unit, the propeller to move the vehicle responsive to the second state of the latch mechanism.

The method can include receiving, by the control unit from a remote computing device, an indication that the cable is decoupled from the vehicle in the flammable fluid. The method can include receiving, by the control unit from a remote computing device, an indication to perform a tank inspection process comprising causing the propeller to move the vehicle to one or more positions in the tank, and determine one or more quality metrics.

At least one aspect is directed to a method of inspecting a tank containing a flammable fluid. The method can include opening a lid of a tank containing the flammable fluid. The method can include connecting a cable to a vehicle. The vehicle can include a battery and a control unit. The method can include lowering, via the cable and through an opening of the tank, the vehicle through a vapor barrier within the tank and on top of the flammable fluid. The method can include disengaging the cable from the vehicle subsequent to the vehicle contacting the floor of the tank. The method can include removing the cable from the tank. The method can include closing the lid of the tank to seal the vehicle in the tank. The method can include performing, via the control unit of the vehicle, a tank inspection process under battery power. The tank inspection process can include generating a map of the tank and determining a quality metric for a portion of the tank corresponding to a location on the generated map.

The method can include initializing, in memory of the vehicle, a map data structure for the tank. The method can include storing, in the map data structure, the map.

The method can include determining, by the control unit upon being lowered in the tank, to generate the map for the tank. The method can include instructing, by the control unit, a ranging device of the vehicle to generate the map for the tank.

The method can include establishing a predetermined duration for the tank inspection process. The method can include storing the predetermined duration in a configuration file in memory of the vehicle. The method can include initiating, by the vehicle responsive to being sealed in the tank and beginning the tank inspection process, a timer based on the predetermined duration. The method can include terminating the tank inspection process responsive to expiration of the timer.

The method can include identifying, by the control unit, an uninspected portion of the tank based on the generated map. The method can include causing, by the control unit, a propeller of the vehicle to move the vehicle towards the identified uninspected portion of the tank.

The method can include identifying, by the control unit, an absence of any uninspected portions of the floor of the tank based on the generated map. The method can include providing, responsive to identifying the absence, an indication that the tank inspection process is complete. The indication that the tank inspection process is complete can include a wireless signal or acoustic signal.

The method can include unreeling, by a winch located external to the tank, the cable to lower the vehicle into the tank. The method can include reeling, by the winch, the cable subsequent to disengaging the cable from the vehicle to remove the cable from within the tank. The method can include unreeling, upon completion of the tank inspection process comprising generating the map of the tank and storing a plurality of indications of the quality metric for the at least one portion of the tank, the cable into the tank. The method can include re-engaging the cable with the vehicle. The method can include reeling the cable re-engaged with the vehicle to remove the vehicle from within the tank.

At least one aspect is directed to a system of inspecting a tank containing a flammable fluid. The system can include a vehicle comprising a battery and a control unit. The system can include a cable connected to the vehicle. The system can include a winch located external to a tank lowering, through an opening of the tank, the vehicle through a vapor barrier within the tank and on top of a flammable fluid contained in the tank. The vehicle can disengage from the cable subsequent to the vehicle contacting the floor of the tank. The winch can remove the cable from the tank. The lid of the tank is closed to seal the vehicle in the tank subsequent to removal of the cable from the tank. The control unit of the vehicle can perform a tank inspection process under battery power, the tank inspection process comprising generating a map of the tank and determining a quality metric for a portion of the tank corresponding to a location on the generated map.

The control unit can initialize, in memory of the vehicle, a map data structure for the tank, and store the map in the map data structure. The control unit can determine, upon the vehicle contacting the floor of the tank, to generate the map for the tank. The control unit can instruct a ranging device of the vehicle to collect data used to generate the map for the tank.

The control unit can retrieve, from a configuration file stored in memory of the vehicle, a predetermined duration for the tank inspection process. The control unit can initiate, subsequent to being sealed in the tank and beginning the tank inspection process, a timer based on the predetermined duration.

The control unit can terminate the tank inspection process responsive to expiration of the timer. The control unit can identify an uninspected portion of the tank based on the generated map. The control unit can cause a propeller of the vehicle to move the vehicle towards the identified uninspected portion of the tank.

The control unit can identify an absence of any uninspected portions of the floor of the tank based on the generated map. The control unit can provide, responsive to identifying the absence, an indication that the tank inspection process is complete. The indication that the tank inspection process is complete can include a wireless signal or an acoustic signal.

The winch can unreel the cable to lower the vehicle into the tank. The winch can reel the cable subsequent to disengaging the cable from the vehicle to remove the cable from within the tank. The winch can unreel, upon completion of a tank inspection process comprising generating the map of the tank and storing a plurality of indications of the quality metric for the at least one portion of the tank, the cable into the tank. The winch can reel, upon the cable re-engaging the vehicle, the cable to remove the vehicle from within the tank.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Following below are more detailed descriptions of various concepts related to, and implementations of, systems, methods and apparatus for inspecting a tank containing a flammable fluid. The various concepts introduced above and discussed in greater detail below may be implemented in any of numerous ways.

This technology is directed to systems, methods and apparatus for inspecting a tank containing a flammable fluid. The system can include an autonomous vehicle having a propeller, battery and control unit. The vehicle, using the control unit, can be self-contained and autonomously inspect the tank. For example, a winch can lower the vehicle into the tank using a cable. While the vehicle is being lowered through the vapor layer over the flammable fluid, the vehicle can remain in a powered off state. The vehicle can include a mechanical pressure switch that detects when the vehicle has been submerged to a predetermined depth into the fluid, and then powers on the vehicle responsive to being submerged to the desired depth. The winch can lower the vehicle to the tank floor, at which point the winch or vehicle can detect that the vehicle is in contact with the tank floor and disengage the cable from the vehicle. Upon being lowered into the flammable fluid in the tank, the vehicle can be disconnected from systems or components external to the tank. The control unit of the vehicle can command the propeller to move the vehicle through the flammable fluid in the tank. While moving throughout the tank, the control unit, using a ranging device, can generate a map of the tank. The control unit can inspect the tank using an inspection device, and store the collected data. The control unit can associate the data from the inspection device with a position or location on the generated map of the tank. By analyzing the collected data, the system can determine the integrity of the tank, such as the thickness of the tank floor, or the level of corrosion of the tank floor.

Thus, systems, methods and apparatus of this technical solution can perform a tank inspection without emptying or draining a flammable fluid from the tank prior to inspecting the tank, thereby improving the efficiency and safety of the tank inspection process, saving time, and utilizing fewer resources. By performing the tank inspection without emptying the flammable fluid, the technology allows for more frequent tank inspections, which can facilitate early detection of tank failures, a more accurate prediction of when the tank may fail, a forecast of the predicted tank integrity.

Figure 1:
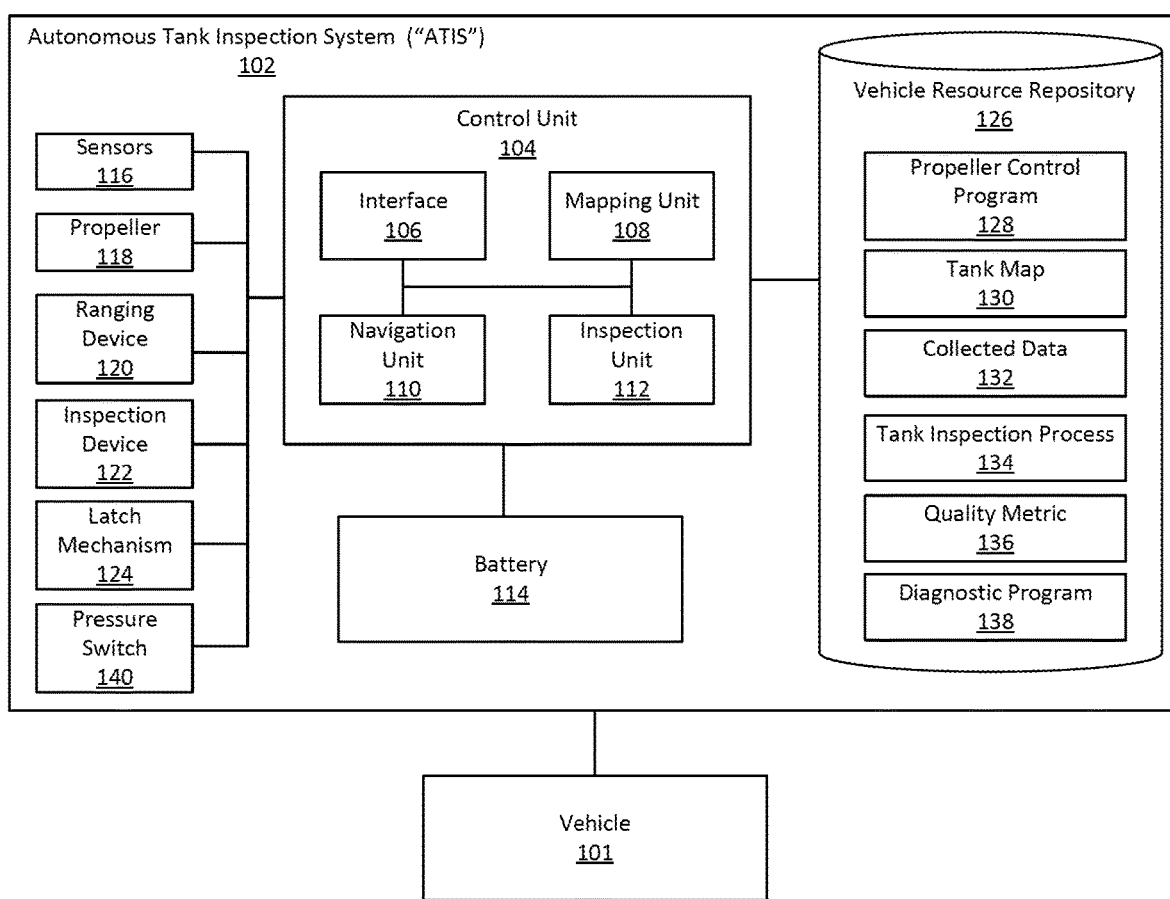
FIG. 1 is a block diagram of an example system to inspect a tank containing a flammable fluid, in accordance with an implementation.

Referring now to FIG. 1, a block diagram of an example system to inspect a tank containing a flammable fluid, in accordance with an implementation, is shown. The system 100 can include a vehicle 101 and an autonomous tank inspection system 102 for performing an autonomous tank inspection. The autonomous tank inspection system ("ATIS") 102 can include at least one control unit 104, at least one battery 114, at least one sensor 116, at least one propeller 118, at least one ranging device 120, at least one inspection device 122, at least one latch mechanism 124, or at least one vehicle resource repository 126. The vehicle resource repository 126 can store software or data associated with the vehicle, including programs, instructions, or data collected by sensors 116. The ATIS 102 can include hardware or a combination of hardware and software, such as communications buses, circuitry, processors, communications interfaces, among others. The autonomous tank inspection system 102 can reside on or within a corresponding vehicle 101.

Each of the components of the ATIS 102 can be implemented using hardware or a combination of software and hardware. Each component of the ATIS 102 can include logical circuitry (e.g., a central processing unit or CPU) that responds to and processes one or more instructions fetched from a memory unit (e.g., memory, storage device, or vehicle resource repository 126). Each component of the ATIS 102 can include or use a microprocessor or a multi-core processor. A multi-core processor can include two or more processing units on a single computing component. Each component of the ATIS 102 can be based on any of these processors, or any other processor capable of operating as described herein. Each processor can utilize instruction level parallelism, thread level parallelism, different levels of cache, etc. For example, the ATIS 102 can include at least one logic device such as a computing device or server having at least one processor.

The components or elements of the ATIS 102 can be one or more separate components, a single component, or a part of the ATIS 102. For example, the control unit 104 (or the other components of the ATIS 102) can include one or more combinations of hardware and software, such as one or more processors configured to initiate stop commands, initiate motion commands, and transmit or receive timing data. The one or more components can work individually external to the ATIS 102.

The one or more component of the ATIS 102 can be hosted on or within a vehicle 101. The components of the ATIS 102 can be connected or communicatively coupled to one another. The connection between the various components of the ATIS 102 can be wired or wireless, or any combination thereof.

The vehicle 101 can include the autonomous tank inspection system ("ATIS") 102 to inspect the tank containing a flammable fluid. The vehicle 101 can include an actuator that locks or unlocks a latch using a latch mechanism 124. The vehicle 101 can include a transducer to transmit a plurality of acoustic signal. The vehicle 101 can be constructed using one or more materials including steel, stainless steel, aluminum, iron, glass, rubber, plastic, or titanium. The vehicle 101 can include one or more wheels and one or more propellers. The wheels can be constructed with one or more materials similar to the vehicle 101. The wheels can be designed as standard/fixed wheel, orientable wheel, ball wheel, Omni wheel, Mecanum wheel, or continuous track. The vehicle 101 can perform one or more tasks by the control unit 104. The tank, the flammable fluid, or the cable can be referred to in FIG. 2A-B or FIG. 3.

In some implementations, the vehicle 101 can be connected to a cable using a latch mechanism 124, which can be used to lower the vehicle 101 through an opening of the tank through a vapor layer within the tank and on top of the flammable fluid. The vehicle 101 can disengage the cable subsequent to the vehicle at least partially submerged in the flammable fluid. The vehicle 101 can then be sealed in the tank, responsive to removing the cable from the tank and closing the lid of the tank. The vehicle 101 can initiate and perform a tank inspection process 134, via the control unit 104, under battery 114 power.

In some implementations, the vehicle 101 can include one or more propellers 118 which can be driven by a motor, but not include any wheels. The wheels may be absent from the vehicle 101 because the one or more propellers can propel or move the vehicle 101 through the flammable fluid in the tank. The vehicle 101 can include one or more wheels driven by a motor. In some cases, the vehicle 101 can include wheels but not a motor to drive the wheels. For example, the wheels may not be motor driven because the propeller 118 can propel or move the vehicle 101 through the flammable fluid in the tank. The vehicle 101 can include one or more fans (e.g. blower fan or axial fan) or heat sinks inside the body that can cool, reduce, maintain, or otherwise manage a temperature of physical components of the ATIS 102.

In some implementations, the vehicle 101 can operate in one or more orientations. The orientations indicating a tilt of the vehicle 101, for example, a 30 degrees tilt or a 180 degrees tilt (e.g. upside down orientation). The one or more wheels can be located at the front, back, side, or bottom of the vehicle, for example. The vehicle 101 can include the one or more wheels on one or more surfaces of the vehicle 101, for example, the wheels can be included on top of the vehicle 101 which can move the vehicle 101 during a reverse or an upside down orientation. The vehicle 101 can configure the one or more wheels located on the one or more surfaces based on the orientation of the vehicle 101.

The vehicle 101 can be coated with non-flammable solution or an insulator. The non-flammable solution or insulator can be applied by spray coating, paint coating, attachment, or sheet cover. The non-flammable solution can include glass, mineral wool, gypsum, or magnesium. The insulator can include glass fiber, polyurethane, clay, or ethylene propylene diene terpolymer ("EPDM") rubber. The vehicle 101 can be coated with linked or merged non-flammable solution and insulator to form a protected layer. The non-flammable solution and insulator can be selected based on the flammable fluid contained inside the tank. The vehicle 101 can incorporate the protected layer for flammable environment, for example, the vehicle can be submerged in the tank containing flammable fluid. The vehicle 101 can be further coated with water resistance solution including durable water repellent ("DWR"). The vehicle 101 coated with DWR can be hydrophobic, which can prevent fluid from entering the vehicle 101. The one or more coating of the vehicle 101 can be coated on the exterior of the vehicle 101 or embedded into the vehicle 101 containing the ATIS 102. The vehicle 101 can operate under mild environment, for example, below freezing temperature or above boiling temperature. The vehicle 101 can operate under submerged environment or on dry environment, such as to perform an in-service tank inspection by submerging the vehicle 101 under the flammable fluid, for example. The vehicle 101 can be re-coated based on the solubility of the coating exposed to the flammable fluid. However, in some cases, the vehicle 101 may not be coated with a non-flammable solution or insulator and perform an in-service tank inspection due to the vehicle 101 using a battery, cable and remaining powered off as the vehicle 101 traverses a vapor layer and until fully submerged in the flammable fluid.

The vehicle 101 can be constructed to prevent sparks or electrostatic discharge. The vehicle 101 can be constructed with one or more insulated layers to prevent sparks or electrostatic discharge. The one or more insulated layers can include a spark protection layer, which can be, for example, a rubber layer between one or more layer of steels, preventing accidental collision between the steel layers which can cause a spark. The vehicle 101 can be equipped with a non-sparking tool or at least one anti-static tool. The non-sparking tool can be characterized by lack of ferrous metals including steel or iron, which can prevent ignition of sparks under certain condition. The vehicle 101 and the ATIS 102 can be grounded by the anti-static tool, which can prevent static electricity build up to cause an ignition. The vehicle 101 can equip the non-sparking tool or the anti-static tool to operate inside the tank containing the flammable fluid, which can prevent the vehicle 101 from igniting sparks caused by grinding one or more vehicle 101 layers or the building up of electrostatic discharge caused by the battery 114 supplying power to the ATIS 102, for example. The vehicle 101 can include housing for the one or more components of the ATIS 102, which can be constructed using similar materials to the vehicle 101. However, grounding the vehicle to a launch and recovery cable at the time of deployment or retrieval may sufficiently discharge any electrostatic charge, and the vehicle 101 may not be further constructed with insulation layers or other coatings or layers to mitigate sparks.

The vehicle 101 can be powered off or enter a low power state or standby state as the vehicle crosses the vapor layer (or vapor gap) above the surface of the flammable fluid. The vehicle 101 can power on or enter an active state after the vehicle is fully submerged (or at least partially submerged) in the flammable fluid. For example, the vehicle 101 can remain powered off until the vehicle 101 is a certain threshold distance under the surface of the flammable fluid (e.g., 1 meter, 2 meters, 3 meters, 4 meters or more). The vehicle 101 can be configured with a pressure switch that can automatically power on the vehicle responsive to detecting that the vehicle 101 has been fully submerged by the threshold distance.

The vehicle 101 can operate under dense flammable environment. The dense flammable environment can include ethanol, gasoline (petrol), diesel, oil, or jet fuel. The vehicle 101 can maintain a temperature lower than an ambient temperature, an autoignition temperature, or a flash point. The autoignition temperature can indicate a temperature point at which a substance can be ignited in normal atmosphere without an external source of ignition. The flash point can indicate the lowest temperature at which vapors of the material will keep burning after an ignition source is removed. For example, gasoline can include an autoignition temperature of 280 Celsius and a flash point of 43 Celsius. The vehicle 101 can use a temperature sensor of the ATIS 102 to indicate the temperature of the vehicle 101, such that the vehicle 101 can initiate an operation condition upon the temperature exceeding certain threshold, for example. The operation condition can lower the speed of the propeller 118, pause the vehicle 101, or stop the vehicle 101 operation. The vehicle 101 can determine the speed of the propeller 118 or inspection time, based on the density of the dense flammable environment. For example, a vehicle submerged in gasoline can determine a first speed of one or more propellers configured for a density of 750 kg/m$^3$, and a second vehicle similar to the first vehicle submerged in diesel can determine a second speed, faster than the first speed, of one or more propellers configured for a density of 830 kg/m$^3$.

The vehicle 101 can monitor the temperature of the vehicle 101 in order to facilitate safely traversing the vapor layer. The vehicle 101 may allow or tolerate a higher temperature when fully submerged in the flammable fluid as compared to when the vehicle 101 traverses the vapor layer located above the flammable fluid during deployment or retrieval operations. For example, the vehicle 101 can allow or tolerate a temperature that may be higher than the flash point of the flammable fluid in the tank while the vehicle 101 is fully submerged in the flammable fluid. However, as the deployment process initiates, the vehicle 101 can reduce or otherwise control the temperature of the vehicle 101 such that the temperature of the vehicle 101 falls below a threshold or desired temperature prior to the vehicle 101 traversing the vapor layer during retrieval. In some cases, the vehicle 101 can maintain the temperature of the vehicle 101 below the flash point of the vapor gap or vapor layer even while the vehicle is fully submerged. In some cases, the vehicle 101 can The vehicle 101 can determine, based on the control unit 104 using a diagnostic program 138, a malfunction of one or more components of the ATIS 102, which can be based on a signal received from the components or a discontinued electrical signal to the components. The vehicle 101 can further determine to use a different component, based on the malfunctioned components, to continue inspecting the tank, for example, the vehicle 101 can determine, based on a malfunctioned propeller 118 due to the propeller 118 not receiving power, to continue the tank inspection using the one or more wheels to drive the vehicle 101, if the vehicle 101 is configured with a propeller 118 and wheels, for example.

The battery 114 can provide power to the vehicle 101 and the components of the ATIS 102. The battery 114 can be embedded into or attached on to the vehicle 101. The battery 114 can include a rechargeable or non-rechargeable type including an alkaline battery, a nickel-cadmium battery, a nickel-metal hydride battery, a lithium-ion battery, or a lead-acid battery. The battery 114 can be recharged using an interface 106 of the control unit 104 of the ATIS 102. The vehicle 101 or battery 114 can be equipped with a temperature sensor. The temperature sensor can determine the temperature of the battery 114, which can indicate a thermal dissipation of the battery 114. The vehicle 101 or ATIS 102 can use the measured or detected temperature of the battery 114 to initiate or change an operation condition associated with the vehicle 101, ATIS 102, tank inspection process or proper control program. Operation conditions can include, for example, an exit condition, waiting condition, low power state, cooling state, or high performance state. For example, the diagnostic program 138 can access the temperature information of the battery 114 and initiate the cooling state based on the temperature reaching a threshold temperature set by the ATIS 102 or initiate the wait condition based on the temperature exceeding the threshold temperature by a predetermined amount. The predetermined amount can be configured prior to the vehicle 101 initiating the tank inspection process 134.

The battery 114 can be embedded inside a housing, which can be constructed with materials similar to the vehicle. The battery 114 can dissipate heat to the housing, such that the housing can dissipate the heat of the battery 114. The housing of the battery 114 can include a temperature sensor, which can indicate the temperature of the housing. The housing temperature can be used to initiate or change an operation condition upon exceeding a temperature threshold of the diagnostic program 138. The temperature threshold can be determined or set based on the type of flammable fluid, such as ethanol, gasoline (petrol), diesel, or jet fuel, a dimension of the tank, the construction of the vehicle 101, or a location of the tank.

The battery 114 can provide an indication of power available to the control unit 104, which can be used by the diagnostic program 138. The indication of power available can be used to determine an operation condition by the diagnostic program 138 of the control unit 104. For example, the power available can be used to determine a speed setting of the propeller 118, such that the ATIS 102 operates on high performance state prior to reaching a first power threshold, operates on low power state based on reaching the first power threshold, or execute the exit condition based on the power available reaching a second power threshold lower than the first power threshold.

The sensors 116 can include a proximity sensor, touch sensor, accelerometer, angular rate sensors, gyroscopes, speed sensor, torque sensor, pressure sensor, temperature sensor, light sensor, electrical charge sensor, electrical current sensor, electrostatic sensor, position sensor, tilt sensor, pitch, roll and heading sensor, or odometer. The sensors 116 can be connected to the battery 114. The sensors 116 can be attached to the vehicle 101 or embedded inside the vehicle 101 such as in front, back, above, side, or underneath the vehicle 101. The sensors 116 can collect one or more information of the vehicle 101 or the ATIS 102 including vehicle speed, propeller torque, component temperature, vehicle travel distance, or vehicle touch information. The vehicle 101 can determine the vehicle state (e.g., accelerations, angular rate, attitude and heading, depth, or position). The sensors 116 can provide data or measurements to the navigation unit 110, which can determine the state of the vehicle 101 (e.g., accelerations, angular rate, attitude and heading, depth, or position).

The vehicle 101 can include a pressure switch 140. The pressure switch can be designed, constructed or configured to close an electrical contact when a certain set fluid pressure has been reached on its input. The pressure switch 140 can be configured to make contact either on pressure rise or pressure fall. The pressure switch 140 can detect mechanical force. The pressure switch 140 can be configured with various types of sensing elements to detect or sense pressure. For example, the pressure switch 140 can include a capsule, bellows, Bourdon tube, diaphragm or piston element that deforms or displaces proportionally to applied or detected pressure. The pressure sensing element of the pressure switch 140 can be arranged to respond to a difference of two pressures. The resulting motion can be applied directly, or through amplifying levers, to a set of switch contacts to power on the vehicle 101 or control unit 104 by closing an electronic circuit between the control unit 104 and the battery 114.

The pressure switch 140 can be configured to operate in flammable fluid by having an enclosure to prevent an arc at the contacts from igniting the surrounding gas. The switch enclosure can be formed of a material that can be non-flammable, weatherproof, corrosion resistant, or submersible.

The pressure switch 140 can close an electrical contact to power the control unit 104 responsive to detecting a threshold pressure. The threshold pressure can correspond to the vehicle 101 being submerged at least 1 meter, 2 meters, 3 meters or more in a fluid. The pressure switch 140 can be designed, constructed or operational to detect the depth based on a known density of the fluid. The pressure can be determined based on P=height*density*acceleration of gravity. The threshold pressure can be set based on determining the desired depth at which the control unit 104 is to be powered on (e.g., 1 meter, 2 meters, 3 meters, or more), the density of the fluid (e.g., 0.7 kg/m$^3$, and gravity (e.g., 9.8 m/s$^2$). The pressure switch 140 can be configured to power on the control unit 104 responsive to detection of the threshold pressure.

The sensors 116 of the vehicle 101 can include a fuel level sensor. In some cases, the vehicle 101 can derive or determine the fuel level via an external fuel level sensor or by not using a separate fuel level sensor. For example, the vehicle 101 can derive the fuel level based on its depth and altitude above the floor. In another example, the vehicle 101 can receive the fuel level information from an external source (e.g., checking the mechanical level gauges installed in or on a tank) prior to deployment into the tank the mechanical level gauges usually installed in tanks. The vehicle 101 can determine the fuel level based on the density of the flammable fluid, the pressure sensor in the vehicle, and an acoustic speed sensor (which can provide altitude above the floor). The vehicle 101 can determine the depth and altitude based on the pressure, which can indicate the liquid level. In some cases, the vehicle 101 can determine the fuel level from a gauge configured on the tank.

The information identified by the sensor 116 can be stored in the collected data 132 within the vehicle resource repository 126, which can be accessed by the control unit 104. The sensor 116 can perform an operation by the control unit 104. The operation can include sensor selection, sensor initiation, or sensor deactivation. The sensor selection can select a sensor 116 from multiple sensors based on one or more commands to be executed by the control unit 104. The sensor initiation can activate at least one sensor 116 to perform the one or more commands, and the sensor deactivation can deactivate at least one sensor 116 upon completing the one or more commands. For example, sensor initiation and deactivation can include selecting the proximity sensor to identify obstruction within the tank for collision avoidance, activating the sensor 116 to obtain proximity data of the tank, and deactivating the sensor 116 upon storing the collected data in the data repository, indicating completion of the one or more commands.

The sensors 116 information can configure or determine a plurality of settings for one or more components of the ATIS 102, for example, using the temperature sensor to determine an operation condition of the vehicle 101. The temperature sensor can be included in or on the battery 114, the propeller 118, or one or more portions of the vehicle 101 to determine the temperature information, wherein the temperature information can be stored in the collected data 132. The temperature sensor can detect changes in temperature based on changes in the one or more substances of the temperature sensor, the changes in the substance can be an expansion or contraction of mercury inside the sensor 116 container. The temperature information can be accessed by the control unit 104 executing the diagnostic program 138 to determine an operation condition of the one or more components of the system 100. The diagnostic program 138 can determine to change the operation condition based on the temperature reaching a first threshold, or to initiate the operation condition based on the temperature reaching a second threshold, for example, the diagnostic program 138, initiating the low power state, decrease the propeller speed based on the temperature of the battery 114 reaching the first threshold and initiate the exit condition to stop the vehicle 101 from executing a command based on the battery 114 reaching the second threshold.

The sensors 116 and the ranging device 120 provide data used by the navigation unit 110 to determine the position of vehicle 101 as it moves along its desired path in the tank 202. The navigation unit 110 can determine or configure the navigation path using the sensors 116. The proximity sensor can be attached or embedded in front of the vehicle 101 to detect nearby object for collision avoidance without physical contact with the object. The proximity sensor can emit an acoustic beam or beam of electromagnetic radiation (e.g., a laser range finding system), and measure travel time to determine the present of one or more objects, which can be referred to as one or more targets. For example, the navigation unit 110, based on the proximity sensor detecting obstruction in close proximity of the vehicle 101, can responsively maneuver the vehicle 101 to avoid collision. A combination of measurements from sensors 116 and the ranging device 120 can be used to determine the vehicle's position over time and generate a map of the tank. For example, the ranging device 120 can determine the position of the vehicle 101 relative to the side of the tank. The ranging device 120 can use sensors 116, or other sensors, for dead reckoning (e.g., the process of determining the position of the vehicle 101 by estimating the direction and distance traveled). In some cases, the sensor 116, such as the odometer, can be used to determine total distance travelled by the vehicle 101. The total distance can be used to generate a map of the tank, determine an operation efficiency of the tank inspection, determine a resource utilization value of the tank inspection, or an amount of power consumed by the vehicle 101 during the tank inspection process. The sensor 116, such as an electrical current sensor, can be used to determine a state of the latch mechanism 124 of the vehicle 101 coupling a cable to the vehicle 101. The state of the latch mechanism 124 can indicate the engagement of the cable to the vehicle 101, which can be based on the flow of current of the latch mechanism 124 detected by the sensor 116. The sensor 116 can detect a first state of the latch mechanism 124 and a second state of the latch mechanism 124 of the vehicle 101 in the flammable fluid. For example, the first state can be the connected state of the latch mechanism 124 and the second state can be the disconnected state of the latch mechanism 124.

The sensors 116 can provide fuel level information using the fuel level sensor embedded in or on the vehicle 101 indicating an amount of fuel remaining in the tank during inspection. The fuel level sensor can include a float, an actuating rod, and a resistor, which can provide a signal indicating the amount of fuel in residing in the tank. The fuel level sensor on the vehicle 101 can provide information to determine a submersion level of the vehicle 101. The submersion level can be used by the control unit 104 to initiate the diagnostic program 138. The fuel level sensor can be used to determine or configure an operation condition based on the tank dimension. The sensors 116 can determine the tilt information using the tilt sensor, indicating the orientation of the vehicle 101. The tilt sensor can be used by the control unit 104 to prevent disorientation of the vehicle 101. Disorientation can refer to the vehicle 101 being upside down, or otherwise oriented in an incorrect or erroneous direction.

The propeller 118 can include a controllable-pitch propeller, skewback propeller, modular propeller, or Voith Schneider propeller. The propeller 118 can be connected to the battery 114. The propeller 118 can use the one or more sensors 116 to determine one or more propeller information including a propeller speed, a propeller torque, or a propeller motor temperature. The propeller information can be stored within the collected data 132 of the vehicle resource repository 126. The propeller 118 can execute one or more commands by the navigation unit 110 of the control unit 104 using the propeller control program 128 stored in the vehicle resource repository 126, which can be based on an execution of a diagnostic program 138. The control unit 104 can increase or decrease the speed of the propeller 118 to adjust the vehicle 101 speed, or change the orientation of the propeller 118 to adjust the direction of the vehicle 101. The control unit 104 can adjust the speed or orientation of the vehicle responsive to or based on the results of executing the diagnostic program 138, or a location of the vehicle 101 on the map of the tank. In some cases, the control unit 104 can disable or turn off the propeller 118 responsive to the results from executing diagnostic program 138. For example, the diagnostic program 138 can identify a failure of a component or an undesired operating condition. The control unit 104, based on the failure or operating condition, can determine not to provide power to the propeller 118. Instead, the control unit 104 can determine to re-run the diagnostic program 138 one or more times until a satisfactory operating condition has been detected.

The propeller 118 can be used to rotate or move the vehicle 101 through the flammable fluid in the tank in one or more directions based on the navigation unit 110 using the propeller control program 128. The propeller 118 can be configured with an operation condition to increase or decrease the propeller speed. In some cases, the propeller 118 can be configured by the diagnostic program 138 to operate in a low power state based on the amount of power or energy remaining in the battery 114. The propeller 118 can operate in a cooling state, based on the temperature information of the battery 114 or the propeller 118. In some cases, the control unit 104 can be configured with a wait condition in which the control unit 104 pauses the propeller 118 responsive to a condition (such as heat buildup or a buildup in electrostatic charge as detected by a sensor 116).

The ranging device 120 can include a bump sensor, infrared sensor, ultrasonic sensor, laser sensor, or radar sensor. The ranging device 120 can be controlled, instructed or managed by the mapping unit 108 of the control unit 104 to execute one or more mapping commands. The ranging device 120 can be connected to the battery 114. The ranging device 120 can provide data to the mapping unit 108 to generate or update a map of the tank based on information from the one or more components of the ranging device 120. The ranging device 120 can collect data used to generate or update the map of the tank based on the vehicle 101 traversing a plurality of portions of the tank. The ranging device 120 can determine, maintain, or update a position of the vehicle 101. The ranging device 120 can be configured by the mapping unit 108 of the control unit 104, for example, to update the position of the vehicle 101. The map of the tank generated by the ranging device 120 can be included, stored, maintained, and updated within a tank map 130 of the vehicle resource repository 126. The mapping unit 108 can use information obtained from any sensors 116 or other sources to generate the map, including, but not limited to, for example the ranging device 120 and sensors 116.

The ranging device 120 can include or use the radar sensor to measure distance between the vehicle 101 and the enclosure of the tank using radio waves with an antenna. The antenna can transmit the radio waves and receive a reflection of the radio waves, the reflection of the radio waves can indicate the enclosure of the tank, which can indicate the dimension of the tank. The dimension of the tank can be stored within the tank map 130. The ranging device 120 can use the ultrasonic sensor to measure the distance between the vehicle 101 and the enclosure of the tank. The ultrasonic sensor can include an ultrasonic element for both emission and reception of ultrasonic waves, the ultrasonic element can emit the ultrasonic waves, initiate a timer, receive the ultrasonic waves, and stop the timer. The ultrasonic sensor can execute a distance measurement technique to determine the distance between the vehicle 101 and the enclosure of the tank. The ranging device 120 can generate the tank map 130 based on acoustic waves reflected off one or more portions of the tank, the acoustic waves generated by the one or more ranging device 120 sensors.

The inspection device 122 can include a magnetic sensor, a magnetic sensor array, an ultrasonic sensor, an ultrasonic array system, an ultrasonic phased array system, or a sweeping device. The inspection device 122 can be connected to the battery 114. The inspection device 122 can be configured by the inspection unit 112 of the control unit 104 to execute one or more commands. The inspection device 122 can inspect the tank to make quality metric measurements, such as measurements related to the thickness or level of corrosion of a portion of the tank. The inspection device 122 can initiate a tank inspection process 134 to make quality metric measurements for portions of the tank. The tank inspection process 134, which can be retrieved from the vehicle resource repository 126, which can be subsequent to the generation of a portion of a tank map 130. The tank inspection process 134 can be based on the result of the diagnostic program 138. The ATIS 102 can store the inspected portion of the tank within the tank map 130 in the vehicle resource repository 126. The inspection device 122 can determine a quality metric 136 of a portion of the tank. The quality metric 136 can include or indicate the thickness of a portion of the tank, or a level of corrosion of a portion of the tank. The vehicle 101 can determine and store the quality metric 136 in the vehicle resource repository 126. The inspection device 122 can execute the inspection process 134 responsive to identifying that a portion of the tank map 130 has not yet been inspected. The inspection device 122 can, however, determine not to execute the inspection process 134 responsive to identifying that the portion of the tank map 130 has already been inspected, thereby reducing computing and energy resource consumption by the vehicle 101.

Figure 3:
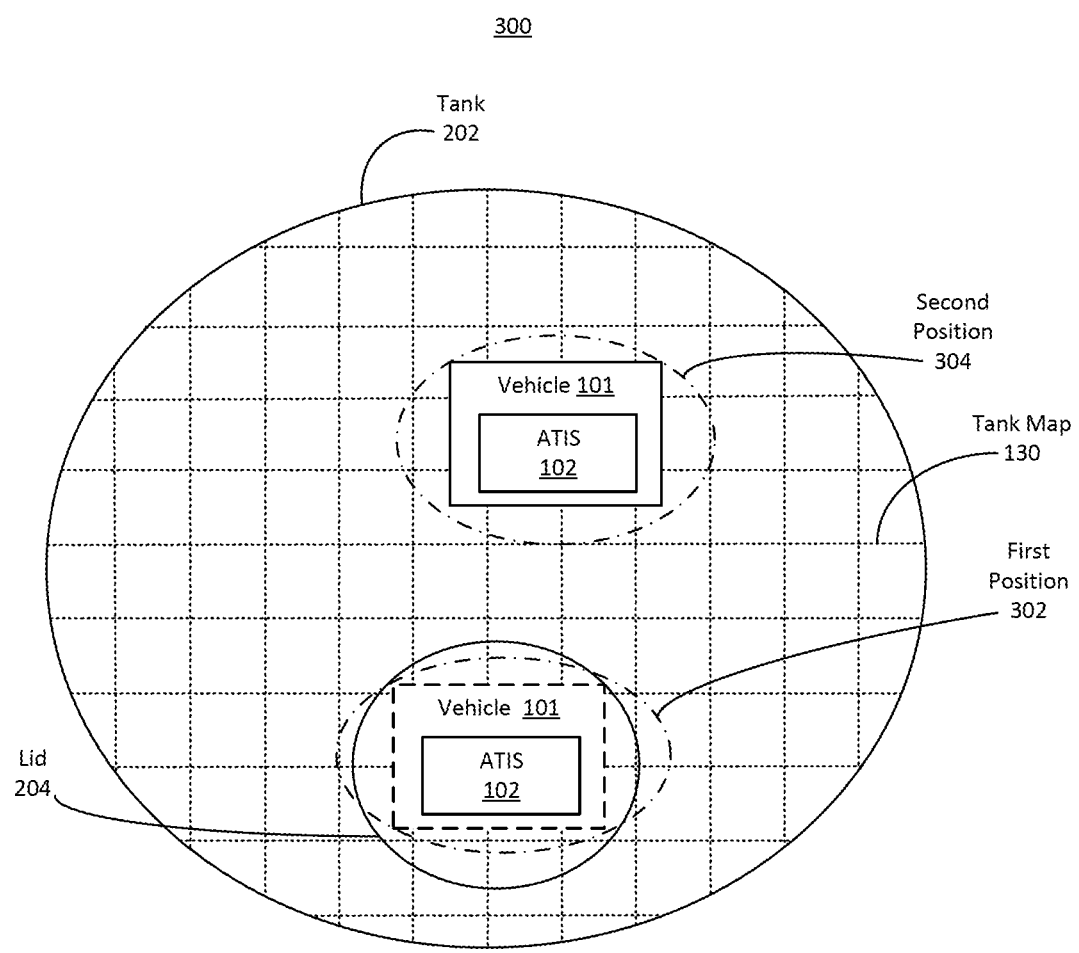
FIG. 3 is an example illustration of a system inspecting a tank containing a flammable, in accordance with an implementation.

The inspection device 122 can use the magnetic sensor or magnetic sensor array to determine the thickness of the tank floor. The magnetic sensor can include one or more coils or one or more conductors that can generate a magnetic field. The inspection device 122 can induce loops of electric current at one or more portions of the tank corresponding to a first position of the vehicle 101 on the tank map 130 (e.g., as illustrated in FIG. 3). The position can refer to a region, area or section of the tank. The control unit 104 can provide instructions or commands to the inspection device 122 to cause the inspection device 122 to modify the magnitude, intensity, or duration of the magnetic field generated by the conductors. For example, the control unit 104, executing the inspection process 134, can generate control commands and output the commands to the inspection device 122.

The inspection device 122 can detect or measure values corresponding to the induced loops of electric current at the one or more portions of the tank. The measured values can correspond to a property of the magnetic field, such as a magnitude, intensity, or decay time, and can be stored in the collected data 132 of the vehicle resource repository 126. The control unit 104 can receive the detected or measured values from the inspection device 122, and process the values to determine a quality metric. The control unit 104 can store the received values as collected data 132 for future processing by the ATIS 102 or an external data process system. To process the values, the inspection unit 112 can use a thickness table (e.g., stored in the vehicle resource repository 126) to convert the measured values associated with the magnitude field to tank floor thickness, which can be stored in the quality metric data structure 136.

The vehicle 101 can include a sweeping device to remove debris that might negatively affect measurements related to the quality metric. For example, the sweeping device can remove substances between the tank enclosure and the inspection device 122 (or sensors 116). The vehicle 101 can measure values after sweeping to obtain an accurate measurement. The vehicle 101 can measure values before and after sweeping to determine the variation or impact on the measurement caused by the debris.

The inspection device 122 can generate pulsed eddy currents to determine the quality metric 136. The inspection device 122 can include a pulsed eddy currents probe to determine a thickness or a corrosion of the tank floor using the pulsed eddy current. The magnetic field can penetrate through the one or more layers or constructions of the tank floor and stabilize in the layer of the tank floor. The electrical current generated by the inspection device 122 can be disabled to cause a drop in the magnetic field, which results in eddy currents appearing in the layers of the tank floor and decreasing strength over time. The pulsed eddy currents probe can be used to monitor the decay in eddy current, the decay can determine the thickness of the tank floor. The electrical current magnitude in a given loop can be proportional to the strength of the magnetic field, the area of the loop, and the rate of change of flux, and inversely proportional to the resistivity of a material.

In some implementations, the inspection device 122 can generate array eddy currents along an array of coils to determine the quality metric 136 at a portion of the tank corresponding to a second position of the vehicle 101 on the tank map 130. The second position can be referred to in FIG. 3. An alternating current can be injected into the coil of the inspection device 122 to create a magnetic field. The inspection device 122 can be placed over the tank floor to generate one or more opposed alternating current. The inspection device 122 can then determine a flaw or corrosion of the tank floor based on the measured distortion of the opposed alternating current.

The inspection device 122 can include an ultrasonic array system or ultrasonic phased array system to determine a second quality metric 136 at the portion of the tank corresponding to the first position of the vehicle 101 on the tank map 130. The second quality metric 136 can be similar to, or different from, the first quality metric 136. The ultrasonic phased array system can include ultrasonic transducers, which can be pulsed independently using computer-calculated timing. Pulsing the ultrasonic transducers can result in steering a beam generated by the ultrasonic transducers to scan the portions of the tank. In some implementations, the inspection device 122 can include two different technologies to generate the quality metric 136 at the portion of the tank. For example, the inspection device 122 can determine a thickness of the tank floor using eddy currents information and a thickness of the tank floor using the ultrasonic phased array information. This allows the vehicle 101 to take advantage of the complementarity of the two technologies. For example, eddy current technology can provide better results compared to ultrasonic technology in the presence of residual sediment after the brush cleans the floor, or in the case the tank floor inside the tank (e.g., topside) is corroded corrosion. Ultrasonic can provide better results as compared to eddy current technology when the floor has been sufficiently cleaned by the brush and is primarily affected by pitting. In some cases, one technology may consume more battery power than another technology, so the vehicle 101 can select a lower power technology in the event the battery level is low in order to prolong the inspection. Thus, the inspection device can include at least two different types of sensors, and select, based on a condition associated with the portion of the tank corresponding to the first position of the vehicle on the map, one of the at least two different types of sensors to inspect the portion of the tank.

Figure 2A:
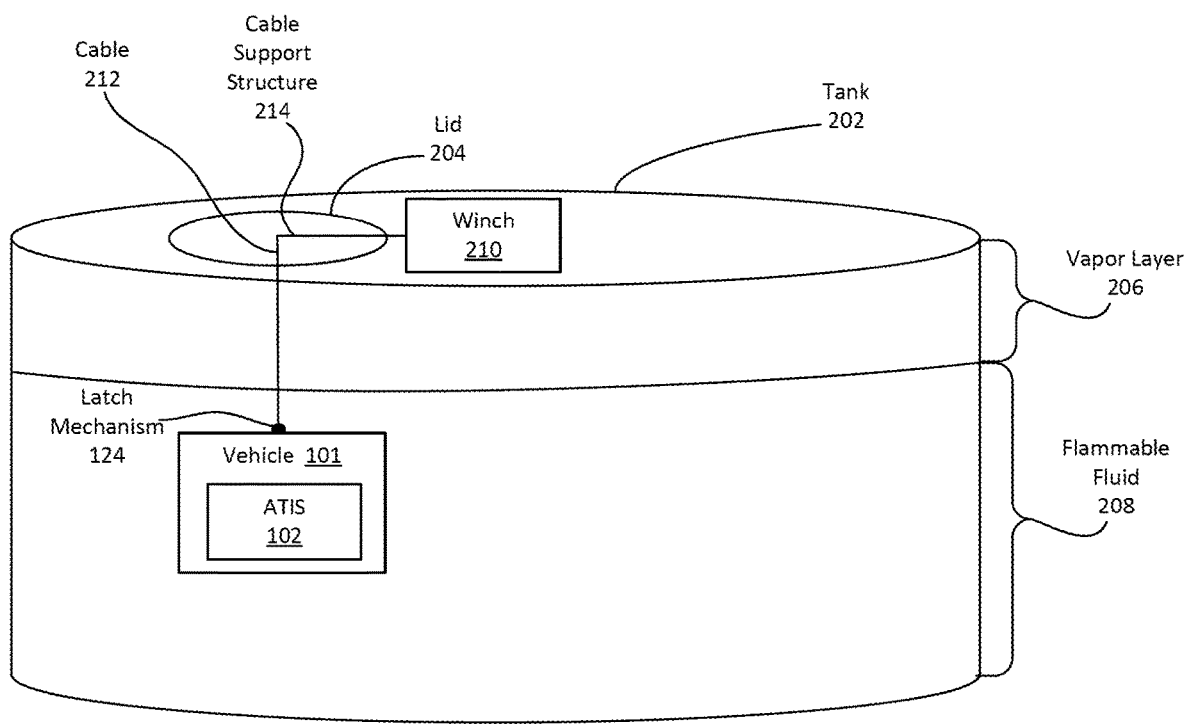
FIG. 2A is an example illustration of a system inspecting a tank containing a flammable, in accordance with an implementation.
Figure 2B:
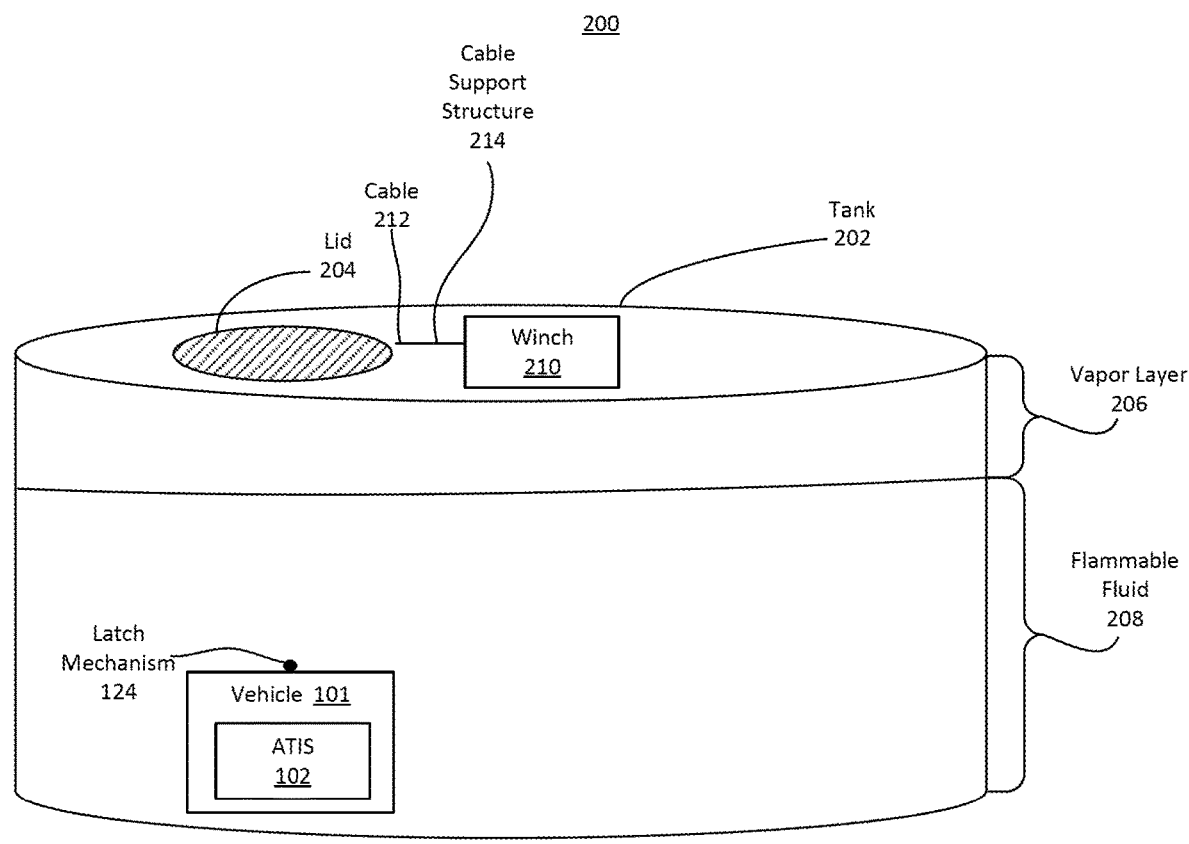
FIG. 2B is an example illustration of a system inspecting a tank containing a flammable, in accordance with an implementation.

The latch mechanism 124 can include a latch detection sensor or a latch lock. The winch can be located external to the tank. The latch mechanism 124 can be connected to the battery 114. The latch detection sensor can determine a state of the latch mechanism 124. The state of the latch mechanism 124 can include a connected state or a disconnected state of the cable 212. The latch mechanism 124 state can indicate the connectivity of the latch, which can be based on a presence or an absence of the latch provided to the control unit 104. The latch detection sensor can include circuitry to determine a latch connection based on an indication of continuous electrical signal. The continuous electrical signal can be provided based on a closed loop connection, which can indicate a connected state of the latch. The disconnection of the latch can be determined based on an absence of the continuous electrical signal. The latch mechanism 124 can be configured by the control unit 104 to execute one or more commands, such as lowering the vehicle 101, by the winch unreeling the cable, into the tank containing the flammable fluid. FIGS. 2A-2B depict an example winch. The latch mechanism 124 can determine to remove the cable from the tank, subsequent to deploying the vehicle 101, for example, reeling the cable subsequent to disengaging the cable from the vehicle 101 to remove the cable form within the tank using the winch. The latch mechanism 124 state can be used by the control unit 104 to determine that a cable used to lower the vehicle into the tank containing the flammable fluid is detached from the vehicle 101. The indication of the detached cable can be provided to the control unit 104 to command the propeller 118 to move the vehicle 101 through the flammable fluid. The latch mechanism 124 can maintain or update the latch mechanism 124 state in the collected data 132 of the vehicle resource repository 126. The latch mechanism 124 can transmit an acknowledgement to the control unit 104 to execute the diagnostic program 138 based on the disconnection of the latch.

The latch mechanism 124 can couple the cable to the vehicle 101 to lower the vehicle 101 into the flammable fluid in the tank using a winch. In some implementations, the latch mechanism 124 can couple the cable to the vehicle 101 to lift the vehicle 101 from the flammable fluid in the tank. The latch mechanism 124 can disengage the cable, based on the vehicle 101 lowered into the tank. The latch mechanism 124 can be locked or unlocked by an actuator of the vehicle 101 connected to the battery 114, the actuator can be configured by the control unit 104. The actuator can unlock the latch mechanism 124 to disengage the cable subsequent to the vehicle 101 lowered into the flammable fluid. The latch mechanism 124 can re-engage the cable to couple the cable to the vehicle 101 based on an exit condition indicated by the inspection process 134, or the diagnostic program 138. The latch mechanism 124 coupling the cable to the vehicle 101 can be controlled by the control unit 104 based on a state of the cable. The latch mechanism 124 state can be used by the control unit 104 to decouple the cable from the vehicle 101 in the flammable fluid based on a first state of the latch mechanism 124 and a policy. The latch mechanism 124 state can be used by the control unit 104 to command the propeller 118 to move the vehicle 101 based on a second state of the latch mechanism 124.

In some implementations, the winch 210 can unreel the cable into the tank upon completion of the tank inspection process 134 comprising generating the map of the tank and storing a plurality of indications of the quality metric 136 for the portion of the tank. The cable can then be re-engaged with the vehicle 101 upon unreeling the cable into the tank using the winch. The winch can then reel the cable re-engaged with the vehicle 101 to remove the vehicle 101 from within the tank.

The vehicle resource repository 126 can include or store the propeller control program 128, the tank map 130, the collected data 132, the tank inspection process 134, the quality metric 136, and the diagnostic program 138. The propeller control program 128 can include or store one or more propeller commands, the propeller commands can determine propeller speed, torque, and orientation, which can adjust the vehicle 101 speed, distance travel, or direction, for example. The propeller control program 128 can be controlled based on the result of the diagnostic program 138 or the state of the cable of the latch mechanism 124. The propeller control program 128 commands can include moving the vehicle 101 through the flammable fluid in the tank. The propeller control program 128 can be used or updated by the navigation unit 110 of the control unit 104 to control the propeller 118.

In some cases, the propeller control program 128 can be configured by the control unit 104 to operate in high performance state based on the available power of the battery 114 or the tank map 130 dimension. In some cases, the propeller control program 128 can operate in low power state based on the available power reaching a first power threshold. In some cases, the propeller control program 128 can initiate an exit condition based on the available power reaching a second power threshold, lower than the first power threshold. In some cases, the propeller 118 can operate in the cooling state, based on the temperature information of the battery 114 or the propeller 118.

The tank map 130 can include, store, or maintain one or more maps of the tank to generate a path for tank inspection or a map data structure to generate a map of the tank. The map data structure can be stored in the data repository 126, which can be part of the tank inspection process 134. The tank map 130 can store information collected from the ranging device 120, which can be configured by the inspection unit 112 of the control unit 104. The tank map 130 can include or store information on the dimension of the tank, or position information of the vehicle 101 corresponding to the map. The dimension information of the tank can include length, width, height, or the circumference or diameter or radius, which can be used by the navigation unit 110 to set the vehicle 101 speed to move in the tank or by the inspection unit 112 using the tank inspection process 134 to set the inspection speed. The tank map 130 can include or store information on one or more inspected portions or one or more uninspected portions of the map. The tank map 130 can be updated by data received from the ranging device 120.

The collected data 132 can include or store data from the sensors 116, the propeller 118, the inspection device 122, the latch mechanism 124, or the battery 114. The sensor data can include the speed of the vehicle 101, speed of the propeller 118, temperature of the vehicle 101 (or portion thereof), temperature of the propeller motor 118, temperature of the battery 114, the travel distance (or position, direction, or heading) of the vehicle 101, the propeller 118 torque, touch information, the magnetic field information, the ultrasonic sensor information, or the latch connection information. The collected data 132 can store acknowledgement feedback from the propeller 118 as a response to the propeller 118 receiving the control instruction. The collected data 32 can store inspection data obtained by the inspection device 122, including magnetic field information and the ultrasonic sensor information to determine a quality metric 136 of the tank enclosure. The collected data 132 can store diagnostic result from executing the diagnostic program 138. The diagnostic result can be used by the control unit 104 to determine whether to initiate the tank inspection process 134, disable the propeller 118 to prevent the propeller 118 from moving the vehicle, or set a speed of the propeller 118. The collected data 132 can include or store latch connectivity information to lower the vehicle 101, via a cable, into the tank containing the flammable fluid, or to remove the cable from the tank, subsequent to deploying the vehicle 101. The collected data can include or store the battery information indicating the power available in the battery 114, the power available can initiate the operation condition by the control unit 104.

The tank inspection process 134 can include or store a plurality of inspection instruction, which can comprise generating the tank map 130 and determining a quality metric 136 for a portion of the tank corresponding to a location on the generated map. The tank inspection process 134 can be configured or used by the inspection unit 112 of the control unit 104 to initiate the inspection device 122. The tank inspection process 134 can be configured based on the result of the diagnostic program 138. The tank inspection process 134 commands can include sweeping instruction for removing sediment on the tank floor, or data collection command for the inspection unit 112 to determine the quality metric 136 of a portion of the tank. The tank inspection process 134 can maintain or update the inspection commands based on the collected data 132 from the inspection device 122, one or more uninspected portions of the tank indicated by the tank map 130, or path of the tank inspection based on the navigation unit 110.

The control unit 104 (e.g., via an inspection unit 112) can retrieve, from the vehicle resource repository 126, a tank inspection process 134. The control unit 104 can load, execute, initiate, run or otherwise perform the tank inspection process 134 retrieved from the vehicle resource repository 126. The tank inspection process 134 can include one or more rules, parameters, conditions, operations, procedures, or other information used to perform a tank inspection. For example, the tank inspection process 134 can include a type of tank inspection, such as an expedient, preliminary, or efficient inspection on one or more portions of the tank floor based on the tank map 130. The tank inspection process 134 can execute a type of inspection based on the size of the tank, tank status, vehicle 101 status, or other condition. An expedient inspection process can reduce the amount of time spent inspecting one or more portion of the tank floor. The expedient inspection process can include increasing the speed at which the vehicle 101 moves through the flammable fluid within the tank, or using a wider track spacing than the length of the inspection device such that the tank floor is not fully covered.

In some implementations, the tank inspection process 134 can maintain or update a predetermined duration (e.g. 30 minutes, 1 hour, 2 hours, etc.) for tank inspection based on one or more inspection unit 112 commands. The predetermined duration can be stored in the tank inspection process 134. The tank inspection process 134 can include a timer based on the predetermined duration. The tank inspection process 134 can be initiated the timer based on the vehicle 101 being sealed in the tank, the timer can provide an indication to terminate the tank inspection process 134 based on the timer reaching the predetermined duration (e.g. expiration of the timer).

The quality metric 136 can refer to values, measurements, or determinations made using collected data 132. The quality metric 136 can be generated by applying one or more processes or techniques to the collected data 132. The processing techniques can include, for example, a thickness measurement technique, thickness table, or corrosion level measurement technique. The quality metric 136 can include or indicate computed thickness information which can be obtained by using the stored collected data 132 from the inspection device 122. The quality metric 136 can maintain and update one or more corrosion level corresponding to the portion of the tank map 130 determined by the inspection device 122. The quality metric 136 can indicate the corrosion level for one or more portions of the tank based on a plurality of tank inspection process 134 performed by the vehicle 101 during a time interval. The quality metric 136 can indicate the corrosion level based on a comparison between the computed thickness information of a first portion compared to a previous inspected thickness information of the first portion, which can be from past inspection, or a second portion thickness information different from the first portion using the thickness table. The thickness table can indicate the standard thickness corresponding to the tank, the standard thickness corresponding to the original thickness of the tank prior to filling the tank with the flammable fluid. The thickness table can include a comparison between magnitude, intensity, or decay time of a magnetic field to the thickness of the tank. The quality metric 136 can include or store a comparison metric, identifying corrosion level difference between the one or more portions of the tank.

The diagnostic program 138 can include or store diagnostic instruction for the vehicle 101. The diagnostic program 138 can include or store one or more instructions to at least test one or more functionalities of the sensors 116, the propeller 118, the ranging device 120, the inspection device 122, the latch mechanism 124, or the battery 114. The diagnostic program 138 can include one or more policies indicating a required condition of the vehicle 101. The required condition can include the vehicle 101 at least partially submerged in the flammable fluid or a successful test of the one or more functionalities of the ATIS 102. The condition can be used by the control unit 104 to provide one or more instructions to the component. The diagnostic program 138 can store one or more diagnostic results in collected data 132 of the vehicle resource repository 126. The diagnostic program 138 can disable the propeller 118 to prevent the propeller 118 from moving the vehicle 101 from a position.

The diagnostic program 138 can provide the one or more diagnostic results to the control unit 104 for determining to initiate the tank inspection process 134, or to initiate the operation condition, which can be based on one or more condition of the ATIS 102 components including the power available in the battery 114, the state of the latch mechanism 124, the sensors 116 information, the propeller 118 information, the ranging device 120 information, or the inspection device 122 information. The diagnostic program 138 can detect the state of the cable, which can indicate the connection of the cable to the vehicle 101. The operation condition can include an exit condition, a wait condition, a low power state, a cooling state, or a high performance state. The exit condition can include one or more commands to move the vehicle 101 towards a first portion of the tank map 130, reel down the cable to the vehicle 101, cause the latch mechanism 124 to re-engage the cable to couple to the cable to the vehicle 101, or terminate vehicle 101 operation. The exit condition can be based on an expiration of a timer of the tank inspection process 134. The wait condition can include one or more commands to hold the vehicle 101 operation which can include movement and sensor activation, or initiate a countdown before executing the vehicle 101 operation. The low power state can include one or more commands to decrease the propeller 118 speed, deactivate one or more sensors 116, or execute a quick tank inspection process 134 which can cover more portions of the tank using the available power of the battery 114. The cooling state can include one or more commands to initiate the propeller 118 inside the body of the vehicle 101 to cool the ATIS 102, decrease execution of the ATIS 102, or hold the vehicle 101 operation based on the temperature. The high performance state can include one or more commands to increase execution of the ATIS 102 which can include activating one or more sensors 116, increasing the propeller 118 speed, or initiating a comprehensive tank inspection process 134.

The control unit 104 of the ATIS 102 can include the interface 106, the mapping unit 108, the navigation unit 110, and the inspection unit 112. The control unit 104 can configure the sensors 116, the propeller 118, the ranging device 120, the inspection device 122, and the latch mechanism 124 using the interface 106, the mapping unit 108, the navigation unit 110, or the inspection unit 112. The control unit 104 can be connected to the battery 114. The control unit 104 can receive an indication of the latch mechanism 124 state from the latch mechanism 124, determine that a cable used to lower the vehicle 101 into the tank containing the flammable fluid is detached from the vehicle 101 based on the latch mechanism 124 state, and command the propeller 118 to move the vehicle 101 through the flammable fluid based on the cable having been detached. The control unit 104 can command the latch mechanism 124 to decouple the cable from the vehicle in the flammable fluid based on the policy and the first state of the latch mechanism 124. The control unit 104 can command the propeller 118 to move based on the second state of the latch mechanism 124, the second state different from the first state.

In some implementations, the control unit 104 can determine to generate the map for the tank based on the vehicle 101 being lowered in the tank. The control unit 104 can then instruct the ranging device 120 using the mapping unit 108 to generate the map for the tank. The map of the tank can be stored in tank map 130. In some implementations, the control unit 104 can identify one or more uninspected portions of the tank based on an absence of indication of inspected one or more portions of the tank map 130. The uninspected one or more portions of the tank can be flagged by the inspection unit 112, the flag can be stored in the tank map 130. The control unit 104 can cause the propeller 118 of the vehicle 101 to move the vehicle 101 towards the identified uninspected portion of the tank. The control unit 104 can initiate the tank inspection process 134 on the uninspected portion using the inspection unit 112. In some implementations, the control unit 104 can identify an absence of any uninspected portions of the floor of the tank based on the tank map 130 generated. The control unit 104 can then provide an indication that the tank inspection process 134 is complete using the exit condition based on identifying the absence of an uninspected portion of the tank. The indication of completing the tank inspection process 134 can comprise an acoustic signal or radio waves.

The interface 106 can include an LCD display, which can include haptic feedback capability for receiving and transmitting information to the control unit 104. The LCD display of the interface 106 can include a graphical user interface which can be used to configure the vehicle 101 setting prior to lowering the vehicle 101 into the flammable fluid. The interface 106 can maintain or update processes of the mapping unit 108, the navigation unit 110, and the inspection unit 112 based on the received or transmitted information. The interface 106 can include one or more ports for external connection to the ATIS 102, such as a serial port, USB port, display port, Ethernet port, or Bluetooth receiver and transmitter. The one or more ports can be used to transfer one or more data to or from the vehicle resource repository 126, such as the propeller control program 128, the tank map 130, the collected data 132, the tank inspection process 134, the quality metric 136, or the diagnostic program 138. The port can be used to charge the battery 114 of the vehicle 101. The interface 106 can be covered by one or more materials for waterproofing.

The mapping unit 108 can provide one or more commands to the ranging device 120, which can be based on the tank map 130, the collected data 132, or the tank inspection process 134. The mapping unit 108 can initiate the map data structure stored in the data repository 126 to generate the map of the tank using the ranging device 120. The mapping unit 108 can be connected to the battery 114. The mapping unit 108 can configure or instruct the ranging device 120 to collect acoustic, electromagnetic radiation, touch or other data associated with the tank. The mapping unit 108 can store the collected data and generate a map of the tank, which can be stored in the tank map 130 located in the vehicle resource repository 126. The mapping unit 108 can determine a first position of the vehicle on the tank map 130. The mapping unit 108 can receive data from the ranging device 120 to generate or update the tank map based on traversing a plurality of points of the tank.

The navigation unit 110 can provide one or more commands to the propeller 118, which can be based on the propeller control program 128, the tank map 130, the operation condition based on the diagnostic program 138 result, or the collected data 132. The navigation unit 110 can configure the propeller 118 to move the vehicle 101 through the flammable fluid in the tank from the first position to the second position, which can be based on the tank inspection process 134. The navigation unit 110 can disable the propeller 118 to prevent the propeller 118 from moving the vehicle 101 from the second position based on the operation condition. The navigation unit 110 can hold the vehicle 101 operation before execution of the diagnostic program 138. The navigation unit 110 can further configure the propeller 118 speed, which can be based on the operation condition, or the location of the vehicle 101. The navigation unit 110 can navigate the vehicle 101 to only the one or more uninspected portions of the tank based on the tank map 130. The navigation unit 110 can navigate the vehicle 101 to cover the entire tank map 130.

The inspection unit 112 can provide one or more commands to the inspection device 122, which can be based on the tank inspection process 134 or the quality of the collected data 132 stored in the vehicle resource repository 126. The inspection unit 112 can identify, based on the collected data 132 using the inspection device 122, the quality of the collected data 132 for the quality metric 136. The quality of the collected data 132 can be based on the inspection device 122, the magnitude of noise obtained by the inspection device 122, or obstruction within the tank, for example, one or more substances covering the tank enclosure can misrepresent the thickness of the tank. The inspection unit 112 can configure the inspection device 122 to inspect the tank based on initiating a tank inspection process 134. The tank inspection process 134 can be based on the operation condition of the diagnostic program 138 result.

The inspection unit 112 can determine the quality metric 136 of a portion of the tank based on the collected data 132 from the inspection device 122, the quality metric 136 indicating a thickness of the portion of the tank at a vehicle 101 position. The quality metric 136 determined by the inspection device 122 can be stored in the vehicle resource repository 126 accessible by the control unit 104. The inspection unit 112 can update the tank inspection process 134 based on the collected data 132, for example, to repeat the tank inspection process 134 on one or more portions of the tank. The inspection unit 112 can re-execute the tank inspection process 134 based on the identified quality of the collected data 132. The inspection unit 112 can configure the inspection device 122 to perform the quick inspection based on the tank map 130 size, or the operation condition, for example, the inspection unit 112 can initiate the quick inspection during the low power state based on the available power of the battery 114 and the one or more uninspected portions of the tank.

Referring now to FIGS. 2A-2B, example illustrations for inspecting a tank containing a flammable fluid, in accordance with some implementations, are shown. The system 200 can include one or more component or functionality of system 100 depicted in FIG. 1. FIG. 2A provides a side view illustration of the tank 202. The system 200 can include a vehicle 101, a tank 202, or a winch 210. The vehicle 101 can include one or more aspects of the vehicle 101 depicted in FIG. 1. The vehicle 101 can include an autonomous tank inspection system ("ATIS") 102 which can comprise one or more aspects depicted in FIG. 1. The tank 202 can include a lid 204, a vapor layer 206, and the flammable fluid 208. The tank 202 can be constructed using one or more materials including metal (e.g. steel, aluminum, alloys, etc.), glass, or plastic (e.g. high-density polyethylene). The lid 204 of the tank can be constructed using the one or more materials similar to the tank 202. The lid 204 can be configured with a locking mechanism to prevent opening of the lid 204 prior to a completion of the tank inspection process 134. The lid 204 can be constructed to seal or keep the vapor layer 206 within the tank 202.

Within the tank 202, and above the surface of the flammable fluid 208, there can be a vapor layer 206. The vapor layer 206 can refer to or include a gaseous state of the flammable fluid 208. The vapor layer 206 can be internal to the tank 202 and above the flammable fluid 208. The vapor layer 206 can be flammable. The vehicle 101 can traverse the vapor layer 206 when the winch 210 lowers the vehicle 101 into the flammable fluid 208, or retrieves the vehicle 101 from the flammable fluid 208.

The winch 210 can include, for example, a snubbing winch, a wakeskate winch, a glider winch, or an air winch. The winch 210 can include a motor, pulley, conveyor, engine, or other mechanism such as a geared hand crank to haul, lift, move or transport the vehicle 101 using a cable 212. The winch 210 can be positioned on the tank 202. The winch 210 can include one or more component depicted in system 400 to control operation of the winch 210. An administrator or user can control the operation of the winch 210.

The cable 212 can include a rope, or wire. The cable 212 can include, or be constructed with, one or more materials such as polyester, nylon, steel, rubber, plastic, cloth, alloys, or wires. To facilitate discharge of potential static build up on the vehicle 101, the cable can be constructed or formed of metal and grounded (e.g., on the topside of the tank).

The cable 212 can be a passive metal cable, or include a copper or fiber optic network cable for receiving or transmitting information to or from the vehicle 101. The cable 212 may not provide any data transfer as the vehicle 101 is deployed and traverses the vapor layer above the flammable fluid, but may transfer data prior to deployment or subsequent to the vehicle 101 being submerged in the flammable fluid. The winch 210 can use the cable 212 to lower the vehicle 101 into the tank 202, or lift the vehicle 101 from the tank 202. The cable 212 can be grounded such that electrostatic charge built up on the vehicle 101 may be discharged when latching on the grounded recovery cable 212. Materials for the cable 212 can be selected to prevent or minimize electrostatic charge build up, or facilitate discharge of electrostatic charge.

The winch 210 can lower the vehicle 101 into the tank 202 with a cable 212. Before lowering the vehicle 101 into the tank, the lid 204 of the tank is opened or removed, thereby creating an opening in the tank 202. The lid 204 can be located on a top portion of the tank 202 such that opening the lid 204 does not result in leakage of the flammable fluid 208. For example, the lid 204 can be located on a portion of the tank 202 that is above a surface of the flammable fluid 208. In some cases, the lid 204 can be temporarily submerged in the flammable fluid 208, but subsequently opened when the level of the flammable fluid 208 falls below an opening that results from opening the lid 204.

To lower the vehicle 101 into the tank 202 containing flammable fluid, the lid 204 can be opened or removed. A cable 212 is connected to the vehicle 101, which can include the ATIS 102. The vehicle 101 can include one or more components depicted in FIG. 1, including, for example, a battery 114 and control unit 104. The cable 212 can be connected to the vehicle 101 using a latch mechanism 124 of the vehicle 101. When using an actuator and sensor, the control unit 104 can receive, from the latch mechanism 124, an indication of the state of the latch mechanism 124. The state can indicate whether the cable 212 is connected to the latch mechanism 124 or the vehicle 101, or whether the cable 212 is disconnected from the latch mechanism 124 or the vehicle 101. The state can indicate a status of the latch mechanism 124, such as whether the latch mechanism 124 is operational or broken. The control unit 104 can lock or unlock, or engage or disengage, the latch mechanism 124 based on the state.

As illustrated in FIG. 2A, vehicle 101 is inserted into the tank 202 through the opening in the tank 202 formed by removing the lid 204. The winch 210 can lower, via the cable 212, the vehicle 101 through a vapor layer 206 within the tank 202 and into the flammable fluid 208. The vapor layer 206 can be located above the flammable fluid 208. The winch 210 can include or use a cable support structure 214 to guide the cable 212 through the lid 204. The cable 212 can be connected to the vehicle 101 via a latch mechanism 124 located on the vehicle 101. The cable support structure 214 can include, for example, a guide rail, conveyor, pipe, pulley, or other supporting structure.

The winch 210 can control one or more aspects related to lowering the vehicle 101 based on a state of the latch mechanism 124. For example, if the cable 212 is connected to the latch mechanism 124, then the state of the latch mechanism 124 can indicate that the cable is connected, engaged, or otherwise coupled to the vehicle 101. The state can be reflected as a binary value, such as 0 or 1, disconnected or connected, standby or active, or open or closed, for example. The latch mechanism 124 can include a sensor 116 or other electronic component that can determine the state of the latch mechanism 124. The vehicle 101 can determine the state of the latch mechanism 124. In some cases, the winch 210 can determine the state of the latch mechanism 124 based on a tension of the cable 212. For example, the tension of the cable 212 may be higher if the cable 212 is connected to the vehicle 101, as compared to when the cable 212 is not connected to the vehicle 101. The vehicle 101 can provide, or the winch 210 can receive or determine, the state of the latch mechanism 124. The winch 210 can determine to lower vehicle 101 into the tank 202 responsive to determining or detecting that the cable 212 is connected to the vehicle 101. The winch 210 can determine to retrieve, raise, or reel up the vehicle 101 responsive to determining or detecting that the cable 212 is connected to the vehicle 101 based on the state of the latch mechanism 124.

FIG. 2B is an example illustration of a system inspecting a tank containing a flammable liquid or fluid, in accordance with an implementation. The vehicle 101 can be lowered through the vapor layer 206 into the flammable liquid 208 using the winch 210 and cable 212. A mechanical pressure switch 140 located in the vehicle 101 can power-up the vehicle 101 when the surrounding pressure is equal to or greater than, for example, 1 meter depth in the flammable fluid, 2 meters depth, 3 meters depth or more. The latch mechanism 124 in the vehicle 101 can disengage the cable 212 after the vehicle 101 has been at least partially submerged in the flammable fluid 208. The control unit 104 can determine not to disengage the latch mechanism 124 from the cable 212 until the vehicle 101 is at least partially submerged in the flammable fluid 208, or not to disconnect until the vehicle 101 has come into contact with the tank floor. The control unit 104 can determine that the cable 212 used to lower the vehicle 101 into the tank 202 containing the flammable fluid 208 is detached from the vehicle 101 based on the disconnected state of the latch mechanism 124.

As illustrated in FIG. 2B, the winch 210 can remove the cable 212 from the tank 202. The winch 210 can remove the cable 212 from the tank 202 responsive to the cable 212 disengaging from the latch mechanism 124 of the vehicle 101. The winch 210 can determine to remove the cable 212 from the tank 202 based on the disconnected state. After the cable 212 has been removed from the tank 202, the lid 204 can close the opening in the tank used to lower the vehicle 101. The lid 204 can seal the tank, thereby preventing the release of any vapor from the vapor layer 206, or the flammable fluid 208. By closing the lid 204, the vehicle 101 can be sealed in the tank 202 without being connected to the winch 210 or any other component or system external to the tank 202. For example, the vehicle 101 may not be physically coupled or connected to any system or component external to the tank 202. The vehicle 101 may not be communicatively coupled to any system or component external to the tank 202 via a cable 212 or wire.

In some implementations, the winch 210 can determine to remove the cable 212 from the tank 202 based on a sensor 116, such as a mechanical force sensor, on the cable 212 indicating a disconnection of the latch mechanism 124 from the cable 212. The sensor 116 on the cable 212 can determine the vehicle 101 was lowered into the flammable fluid 208 based on the difference of forces measured by the sensor 116. For example, the sensor 116 can measure a 1000N force prior to lowering the vehicle 101 into the tank, measure a 50N force when the vehicle 101 is fully submerged in the flammable fluid 208 prior to reaching the tank 202 floor, and measure a 10N force when the vehicle 101 rests on the tank 202 floor. Once the latch mechanism 124 detaches the vehicle 101 from the cable 212, the force measure by the force sensor 116 goes to near 0. The winch 210 can then determine, based on the difference between the forces measured by the sensor 116, to reel up the cable 212 based on the vehicle 101 being at least partially submerged and detached from the cable 212 in the flammable fluid 208 or the vehicle 101 resting on the tank 202 floor and detached from the cable 212. The winch 210 can further determine to remove the cable 212 from the tank 202 based on a timer. The timer can be predetermined based on a historical data 420 indicating a time for the vehicle 101 to be lowered into the tank 202 and disconnect the cable 212 from the latch. The historical data 420 can be referred to in FIG. 4.

The vehicle 101 can perform the tank inspection process 134 using power provided by the battery 114. The battery 114 can provide power to one or more component of the vehicle 101, including, for example, the control unit 104, sensors 116, propeller 118, ranging device 120, inspection device 122, latch mechanism 124 or data repository 126. The control unit 104 can execute a tank inspection process 134 to inspect the tank. The tank inspection process 134 can include instructions to generate a map of the tank 202 or to determine a quality metric 136 for a portion of the tank 202 corresponding to a location of the generated tank map 130. The control unit 104 can perform or execute the one or more instructions of the tank inspection process 134 when the vehicle 101 is at least partially submerged, or fully submerged, in the flammable fluid 208. The control unit 104 can determine not to perform the tank inspection process 134 based on the state of the latch mechanism 124. For example, if the state of the latch mechanism 124 indicates that the cable 212 is still connected to the vehicle 101, the control unit 104 can determine not to initiate the tank inspection process 134, or otherwise abort or terminate the tank inspection process 134.

The control unit 104 can determine to not initiate, abort or terminate the tank inspection process if the lid 204 of the tank is open. The control unit 104 can receive an indication of whether the lid 204 is open or closed, or otherwise detect or determine whether the lid 204 is open or closed. For example, a sensor 116 (such as a light sensor or optical sensor) of the vehicle 101 can determine whether the lid 204 is open or closed by detecting a light source or an ambient light level in the tank 202. If the ambient light level is greater than or equal to a threshold, then the vehicle 101 can determine that the lid 204 is open. If the ambient light level is less than or equal to a threshold, then the control unit 104 can determine that the lid 204 is closed. Responsive to determining that the lid 204 is closed, the control unit 104 can command the propeller 118 to move the vehicle 101 through the flammable fluid 208. The vehicle 101 can determine that the cable has been detached from the vehicle 101 based on determining that the lid 204 is closed. The control unit 104 can determine generate a portion of the map 130 of the tank, and determine, via the inspection device 122, a quality metric 136 for the portion of the tank 202 corresponding to the portion of the map 130.

FIG. 3 is an example illustration for inspecting a tank containing a flammable fluid, in accordance with an implementation. The system 300 can include one or more component or functionality depicted in FIG. 1, 2A or 2B, including, for example, a vehicle 101 or a tank 202. FIG. 3 depicts a top view of the tank 202. The vehicle 101 can include one or more aspects of vehicle 101 of system 100 depicted in FIG. 1. The vehicle 101 can include an autonomous tank inspection system ("ATIS") 102 which can comprise one or more aspects depicted in FIG. 1. The vehicle 101 can generate a tank map 130, which can be represented in the illustration 300. The tank 202 can include a lid 204 or other aspects depicted in FIG. 2A-B. The system 300 can include an inspection device 122 of the vehicle 101, which can be electrically connected to the control unit 104 and the battery 114. The inspection device 122 can receive a command to initiate an inspection at the first position on the tank map 130 from the control unit 104 responsive to the ranging device 120 identifying a first position 302 of the vehicle 101 on the tank map 130. The inspection device 122 can be configured by the tank inspection process 134. The first position 302 can indicate the position of the lid 204 with respect to the tank 202, the lid 204 used for lowering the vehicle 101 into the tank 202. The control unit 104 can move the vehicle 101 to the first position 302 based on an initiation of an exit condition.

The system 300 can include the vehicle 101 located within the tank 202. The vehicle 101 can include the inspection device 122. The inspection device 122 can include one or more conductors. The vehicle 101 (e.g., via the inspection unit 112) can command the inspection device 122 to change a magnetic field generated by the one or more conductors to induce loops of electric current that extend towards a portion of the tank 202 corresponding to the first position 302 on the tank map 306. The vehicle 101 (e.g., via the inspection unit 112) can then detect or receive one or more values corresponding to the induced loops of electric current at the portion of the tank 202 corresponding to the first position 302 on the tank map 306. The one or more values can include a magnitude, amplitude, intensity, flux, flux density, decay time, or direction of the magnetic field, which can indicate the thickness of the tank 202. The magnitude or the direction of the magnetic field can correspond to the direction of the induced loops of electric current or magnitude of the electric current. The magnitude of a magnetic field can be provided in teslas ("T"), the flux of the magnetic field can be provided in webers ("Wb"), and the flux density can be provided as Wb/square meter.

Figure 4:
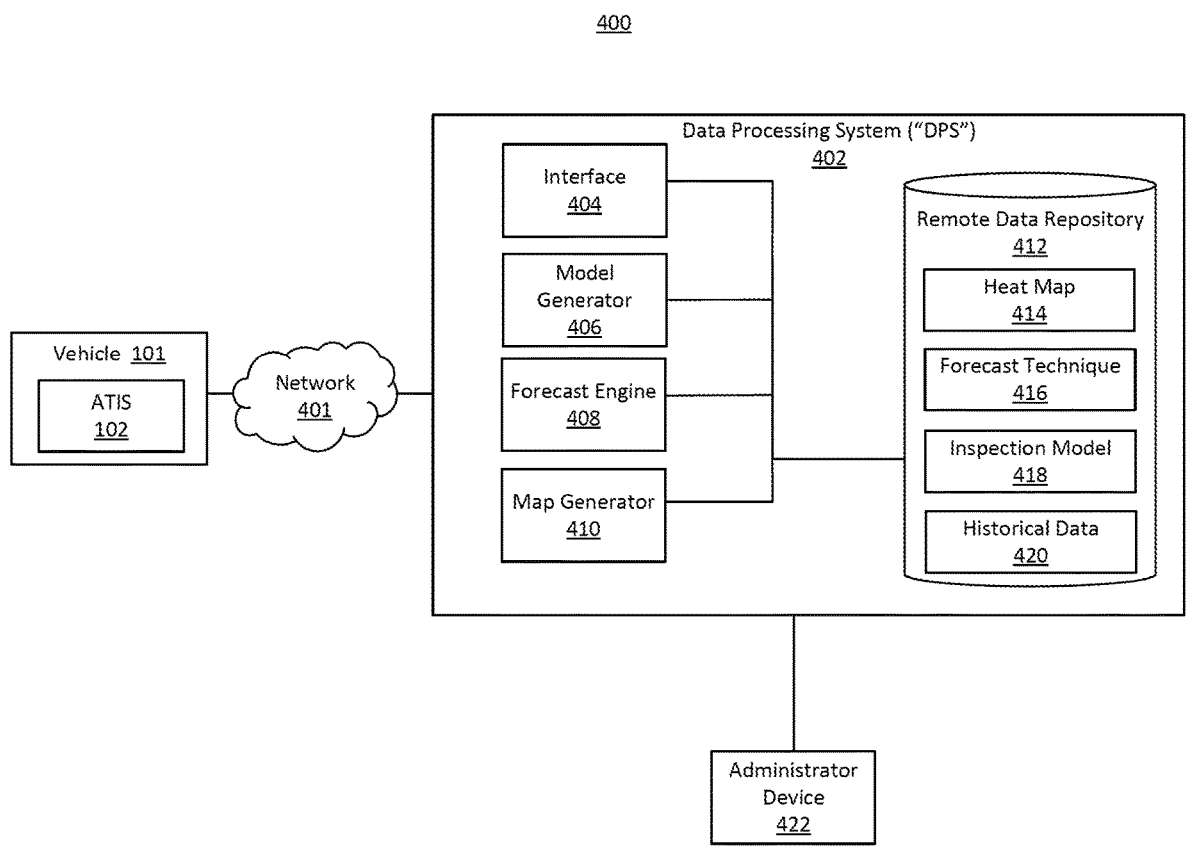
FIG. 4 is a block diagram of an example system to facilitate a tank inspection.

FIG. 4 is a block diagram of an example system to perform a tank inspection. The system 400 can include one or more component or functionality of system 100 depicted in FIG. 1. The system 400 can include a vehicle 101, network connection 401, data processing system ("DPS") 402, or administrator device 422. The vehicle 101 can include an autonomous tank inspection system ("ATIS") 102 which can include at least one aspect depicted in FIG. 1. The vehicle 101 can be connected to the network 401 via wired or wireless connection. The vehicle 101 can be disconnected from the network 401 and operate independent from the data processing system 402. The vehicle 101 can access information from the data processing system 402 via the network 401. The data processing system 402 can be updated or configured by the administrator device 422. The administrator device 422 can be connected wired or wireless to the data processing system 402.

The network 401 can include or refer to a wired or wireless connection, communication, or transfer of information. The network 401 can include computer networks such as the Internet, local, wide, metro, or other area networks, intranets, satellite networks, and other communication networks such as voice or data mobile telephone networks. The network 401 can include a wired connection or communication using, for example, USB, Ethernet, serial port, digital subscriber line ("DSL"), cable, or fiber. The network 401 can transmit information to or receive information from the vehicle 101 via the interface 106 of the vehicle 101.

The network 401 can be any type or form of network and can include any of the following: a point-to-point network, a broadcast network, a wide area network, a local area network, a telecommunications network, a data communication network, a computer network, an ATM (Asynchronous Transfer Mode) network, a SONET (Synchronous Optical Network) network, a SDH (Synchronous Digital Hierarchy) network, a wireless network and a wireline network. The network 401 may include a wireless link, such as an infrared channel or satellite band. The topology of the network 105 may include a bus, star, or ring network topology. The network may include mobile telephone networks using any protocol or protocols used to communicate among mobile devices, including advanced mobile phone protocol ("AMPS"), time division multiple access ("TDMA"), code-division multiple access ("CDMA"), global system for mobile communication ("GSM"), general packet radio services ("GPRS") or universal mobile telecommunications system ("UMTS"). Different types of data may be transmitted via different protocols, or the same types of data may be transmitted via different protocols.

The data processing system 402 can include an interface 404, a model generator 406, a forecast engine 408, a map generator 410, or a remote data repository 412. The data processing system 402 can include hardware or a combination of hardware and software, such as communications buses, circuitry, processors, communications interfaces, among others, similar to the ATIS 102. The data processing system 402 can be connected to the vehicle 101 via the network 401. The data processing system 402 can be connected to the network 401 via a wired or wireless connection.

Each of the one or more components of the data processing system 402 can be implemented using hardware or a combination of software and hardware. Each component of the data processing system 402 can include logical circuitry (e.g., a central processing unit or CPU) that responses to and processes one or more instructions fetched from a memory unit (e.g., memory, storage device, or remote data repository 412). Each component of the data processing system 402 can include or use a microprocessor or a multi-core processor. A multi-core processor can include two or more processing units on a single computing component. Each component of the data processing system 402 can be based on any of these processors, or any other processor capable of operating as described herein. Each processor can utilize instruction level parallelism, thread level parallelism, different levels of cache, etc. For example, the data processing system 402 can include a logic device such as a computing device or server having at least one processor.

The one or more components or elements of the data processing system 402 can be one or more separate components, a single component, or be part of the data processing system 402. For example, the model generator 406 (or the other components of the data processing system 402) can include one or more combinations of hardware and software, such as one or more processors configured to initiate model generation commands, initiate update model commands, and transmit or receive the model information. The one or more components can work individually external to the data processing system 402.

The one or more component of the data processing system 402 can be configured or updated by the administrator device 422. The one or more components of the data processing system 402 can be connected or communicatively coupled to one another. The connection between the various components of the data processing system 402 can be wired or wireless, or any combination thereof.

The interface 404 of the data processing system 402 can include one or more ports for connecting to the network 401 or the administrator device 422. The one or more ports can include, for example, a serial port, USB port, Ethernet port, or Bluetooth receiver and transmitter. The interface 404 can transmit or receive one or more remote data repository 412 information to or from the vehicle 101 or the administrator device 422. The information of the remote data repository 412 can include a heat map 414, a forecast technique 416, an inspection model 418, and historical data 420. The interface 404 of the data processing system 402 can be similar to the interface 106 of the ATIS 102. For example, the interface 404 can be provided with one or more inspection information by the vehicle 101 to store or update the historical data 420. The interface 404 can be provided with one or more previous inspection information from a plurality of tanks 202 inspection by the administrator device 422 to update the historical data 420.

The model generator 406 can generate a risk-based inspection model 418 based on a time-series of quality metrics 136 determined based on ultrasonic thickness data or the loops of electric current provided by the inspection device 122 that extend towards one or more portions of the tank 202. The inspection model 418 can be stored in the remote data repository 412. In some implementations, the quality metric 136 can only store one or more raw information of the tank 202 based on the information from the inspection device 122. The model generator 406 can access or utilize the historical data 420 of the tank 202, the historical data 420 comprising one or more information of the quality metrics 136 from one or more past inspection of various tanks 202. The model generator 406 can generate a model based on a forecast of the forecast engine 408 using the forecast technique 416. The forecast can provide an indication of predicted one or more level of thickness of the tank 202 based on one or more information of the historical data 420.

The model generator 406 can aggregate one or more historical quality metrics 136 from the historical data 420 obtained from a plurality of tank inspections to forecast a level of thickness of the tank 202 based on the quality metric 136. The historical quality metrics 136 indicating one or more thickness level of the tank 202. The forecast thickness level of the tank 202 can indicate the risk of leakage of the tank 202, the risk can be provided to the administrator device 422. For example, a plurality of quality metrics 136 of the tank 202 obtained from year 2018 can be aggregated with a quality metric 136 of the tank 202 obtained from year 2019 using the forecast engine 408. The forecast engine 408 can utilize the forecast technique 416 to indicate a deterioration rate of the tank 202, which can be based on the difference between the 2019 quality metric and the 2018 quality metric. The model generator 406 can receive the indication of the deterioration rate of the tank 202 and generate a risk-based inspection model 418 which can indicate a time leakage will occur in one or more portions of the tank 202.

Inputs to the risk-based inspection model 418 can include original design and construction drawings as well as information about the quality of the materials and fabrication techniques (e.g., welding) used to build the tank, which can provide a baseline for future inspections. A record of operating conditions can allow verification that the tank was operated within its functional limits (e.g., max fill level). A history of tank floor quality metrics, recorded during previous inspections, can be used as the primary driver to establish deterioration trends using a variety of models associated with different types of deteriorations (for instance general, local or pitting corrosion). The forecast engine 408 can perform risk analysis by determining the probability of failure, which is then converted into a period of time after which the tank should be taken out of service for repairs. The forecast engine 408 can assess the probability of failure based on a qualitative approach (engineering/expert judgement and experience using qualitative terms such as very unlikely, unlikely, possible, probable, or highly probable), a semi-qualitative approach (modification of the nominal floor failure frequency—if available—by factors specific to the particular floor's management and environment) or a quantitative approach (structural reliability analysis method). The output of the model can include a period of time the tank can remain in service until the tank should be taken out of service for repairs. Thus, the model generator 406 can generate a risk-based inspection model based on a time-series of quality metrics (e.g., determined based on the loops of electric current provided by the inspection device that extend towards the portion of the tank), and aggregate the historical quality metrics obtained from a plurality of tank inspections to forecast a level of thickness of the tank based on the quality metric.

The forecast engine 408 can access one or more forecast techniques 416 to perform a risk prediction of the tank 202. The risk can indicate a corrosion level of the tank 202, an indication of the tank 202 thickness over time, or a leakage time of the tank 202. The risk can be determined based on a historical quality metric 136, a historical flammable fluid level, or a historical environment of the tank 202. The historical quality metric 136 can indicate one or more thickness levels of the tank 202 from one or more past inspection. The historical flammable fluid level can indicate a plurality of periodic flammable fluid levels of the tank 202 based on flammable fluid level information provided by the administrator device 422, or the historical data 420 including flammable fluid level information from a previous inspection of the tank 202. The historical environment or an environmental information of the tank 202 can indicate a plurality of periodic information based on atmospheric information (e.g. gases and other atmospheric particles) or a climate information provided by the administrator device 422 or the historical data 420 comprising one or more environmental conditions (e.g. temperature, humidity, etc.) of the tank 202 based on one or more past inspection. The forecast engine 408 can generate a graph to indicate a corrosion rate based on one or more historical data 420 containing a plurality of quality metric 136 from a plurality of inspections, the graph can be a time to thickness comparison. The quality metric 136 from the historical data 420 can be one or more points on the graph, for example, the forecast engine 408 can use a first quality metric 136 from an inspection of the tank 202 performed in the year 2010 and a second quality metric 136 from an inspection performed in the year 2015 to generate a line on the graph illustrating a linear rate of decay of the tank 202. The forecast engine 408 can further use the plurality of quality metric 136, such as 50 quality metrics 136 over a time, to predict a time interval for leakage based on the condition of the tank 202. The condition of the tank 202 can include a geographical location of the tank 202, a fuel level contained in the tank 202, or a current thickness of the tank 202. In some implementations, the graph can display a linear decay rate based on the tank 202 thickness from 20 cm to 15 cm and an exponential decay rate based on the tank thickness from 15 cm to 0 cm.

The map generator 410 can generate a heat map 414 of the tank 202 based on the quality metric 136 of the one or more portions of the tank 202. The map generator 410 can initiate a generation of the heat map 414, based on the vehicle 101 providing the tank map 130 and the quality metric 136 to the data processing system 402 via the network 401. The map generator 410 can aggregate the tank map 130 information and the quality metric 136 information to generate a heat map 414 indicating one or more levels of thickness of a plurality of portions of the tank 202 using a plurality of color codes. The plurality of color codes can range from red to green to blue. For example, a very thick portion of the tank 202 can be color coded with blue, a very thin portion of the tank 202 can be color coded with red, and a spectrum of color between the blue and the red can indicate the gradual increase or decrease of the thickness of the one or more portions of the tank 202. The map generator 410 can generate a 2-D heat map 414 or a 3-D heat map 414 of the tank 202 indicating the thickness of the plurality of portions of the tank 202.

The remote data repository 412 can include the heat map 414, the forecast technique 416, the inspection model 418, or the historical data 420. The remote data repository 412 can include storage (e.g. hard disk drives, solid state drives, floppy disks, magnetic tape, etc.) which can store tank information including information associated with previous inspections of one or more tanks. The remote data repository 412 can store environmental information. The environmental information can include, for example, atmospheric information (e.g. pressure, gases, atmospheric particles), climate information (e.g. temperature, humidity, radiation, and amount of rain), topographic information, altitude information, ground information, or subsurface information. The data processing system 402 can obtain the environmental information from the vehicle 101. The data processing system 402 can obtain the environmental information from external sources or databases. The administrator device 422 can provide the environmental information to the data processing system 402.

The heat map 414 can include or store a plurality of color coded tank maps 130 of the tank 202 generated by the map generator 410. The color code can range from red to green to blue. The heat map 414 can utilize the plurality of color codes to provide a graphical representation of the tank map 130 indicating the thickness level of the tank 202. For example, a very thick portion of the tank 202 can be color coded with blue, a very thin portion of the tank 202 can be color coded with red, and a spectrum of color between the blue and the red can indicate the gradual increase or decrease of the thickness of the one or more portions of the tank 202. The heat map 414 can indicate the texture of the tank 202 based on the thickness level information. The texture of the tank 202 can represent one or more bumps or one or more dips of the tank 202. The plurality of color code can be configured by the administrator device 422. The heat map 414 can be provided to the administrator device 422 to display the graphical representation of the tank map 130. The heat map 414 can store a 2-D heat map 414 or a 3-D heat map 414 of the tank 202 generated by the map generator 410.

The forecast technique 416 can include a plurality of time-series forecasting techniques for determining a risk-based inspection model 418. The forecast technique 416 can be accessed or used by the forecast engine 408. The risk can represent a deterioration rate of the tank 202 based on the difference between present and one or more past tank 202 thickness level, the environmental information, or the historical data 420. The risk can further represent a predicted leakage time of the one or more portions of the tank 202 or the indication of one or more thickness level of the tank 202 over time. The predicted time of leakage can be based on the present thickness level of the one or more portions of the tank 202 and the corrosion rate of the tank 202. The forecast technique 416 can be assisted by a machine learning technique or one or more information from the administrator device 422.

The inspection model 418 can store a plurality of risk-based model based on the time-series of quality metrics 136 generated by the model generator 406. The inspection model 418 can be a human readable report. The inspection model 418 can be provided to the administrator device 422 indicating the corrosion rate of the tank 202, at least an indication of the tank 202 thickness over time, or the predicted time of leakage of the tank 202. The inspection model 418 can be presented in a graphical format or a table. For example, the inspection model 418 can be generated and stored in the remote data repository 412 by the model generator 406. The inspection model 418 can be accessed and obtained by the administrator device 422 to display an inspection model 418, which can include the indication of the corrosion rate, the thickness over time, or the predicted time of leakage of the tank 202. The inspection model 418 can be used by the administrator device 422 to identify a maintenance time for one or more portions of the tank 202, at least an inspection cycle for the tank 202, or at least an indication of occurring leakage of the tank 202. The occurring leakage of the tank 202 can be based on an absence of one or more portions of the tank 202 identified by the inspection device 122.

The historical data 420 can include or store one or more quality metrics 136 which can indicate the thickness level of the tank 202. The historical data 420 can include or store a plurality of quality metrics 136 from one or more previous inspections of a plurality of tanks 202. Each tank 202 of the plurality of tanks 202 can be different in at least dimension, construction, or location. The historical data 420 can include or store a flammable fluid level of the tank 202, dimensions of tank 202, or the environmental information of the tank 202. The environmental information can include atmospheric information (e.g. gases and other atmospheric particles) or an environmental condition (e.g., temperature, humidity, pressure, or altitude) of the tank 202. The historical data 420 can be obtained, configured, or updated by the administrator device 422. The historical data 420 can be accessed by the forecast engine 408 or the model generator 406 for generating an inspection model 418. The vehicle 101 can receive historical data via a network.

The administrator device 422 can include an interface 404 similar to the data processing system 402 or the ATIS 102. The interface can include an LCD display, serial port, USB port, display port, Ethernet port, or Bluetooth receiver and transmitter. The administrator device 422 can be connected to the data processing system 402 via wired or wireless connection to the interface 404 of the data processing system 402. The administrator device 422 can be remote to the data processing system 402. The administrator device 422 can configure or update one or more components of the data processing system 402 which can include the model generator 406, the forecast engine 408, the map generator 410, or the remote data repository 412.

The administrator can be provided with a risk-based inspection model 418 based on a time-series of quality metrics 136, the inspection model 418 can be displayed on the administrator device 422 illustrating one or more risk of the tank 202 including the corrosion rate of the tank 202, at least an indication of the tank 202 thickness over time, or the predicted time of leakage of the tank 202. The inspection device 422 can update the historical data 420 with one or more quality metrics 136 of a plurality of tanks 202 via the interface 404. The administrator device 422 can update the historical data 420 with one or more environmental information of the tank 202. The administrator device 422 can provide one or more settings to adjust one or more color codes of the heat map 414 or adjust a type of heat map 414 to generate (e.g. 2-D or 3-D). The administrator device 422 can update the forecast technique 416 based receiving a different technique for forecasting. The administrator device 422 can identify a maintenance time for one or more portions of the tank 202, an inspection cycle for the tank 202, or an indication of occurring leakage of the tank 202 based on the inspection model 418.

Figure 5:
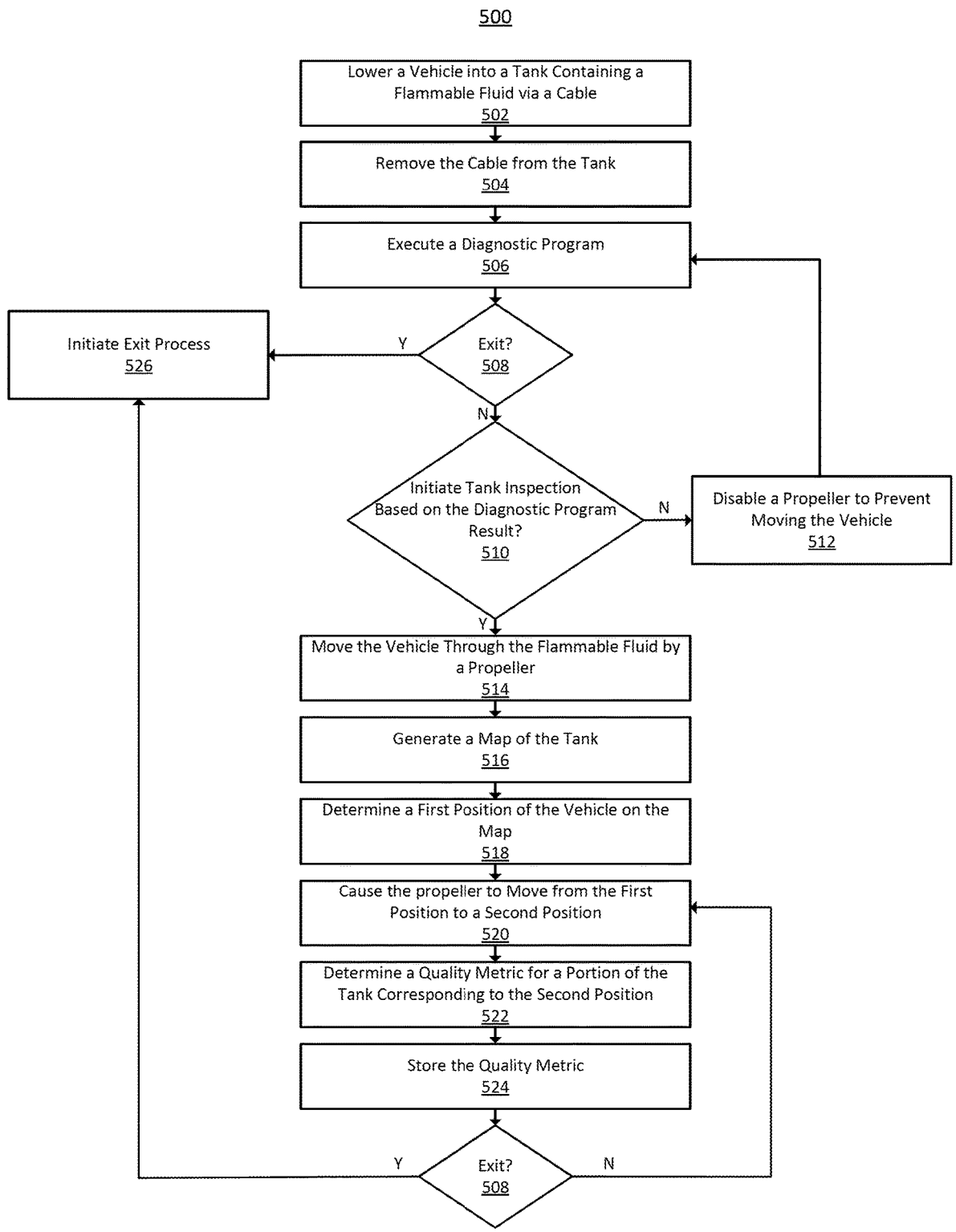
FIG. 5 is a flow diagram of an example method of inspecting a tank containing a flammable fluid.

FIG. 5 is a flow diagram of an example method of inspecting a tank containing a flammable fluid. The method 500 can be performed by system 100, system 400, or one or more component thereof. In brief overview, at step 502, a winch can lower at least one vehicle into the tank containing flammable fluid via a cable. At step 504, the winch can remove the cable from the tank. At step 506, the vehicle can execute the diagnostic program. At step 508, the vehicle can determine to initiate an exit process based on the diagnostic program result. At step 510, the vehicle can determine to initiate a tank inspection process based on the diagnostic program result. At step 512, the vehicle can disable the propeller to prevent moving the vehicle. At step 514, the vehicle can move through the flammable fluid by a propeller. At step 516, the vehicle can generate a map of the tank. At step 518, the vehicle can determine a first position of the vehicle on the tank map. At step 520, the vehicle can cause the propeller to move from the first position to a second position. At step 522, the vehicle can determine a quality metric for at least one portion of the tank 202 corresponding to the second position. At step 524, the vehicle can store the quality metric 136 in the vehicle resource repository. At step 526, the vehicle can initiate the exit process based on an exit condition from the diagnostic program result.

Still referring to FIG. 5, and in further detail, a winch can lower a vehicle 101 into the tank containing flammable fluid via a cable at step 502. The vehicle can include a control unit, battery, sensor, propeller, ranging device, inspection device, latch mechanism, or vehicle resource repository. The cable of the winch can be connected to the vehicle via the latch mechanism. The latch mechanism can be configured by the control unit to receive an indication of a state of the latch mechanism, the state can indicate the connection of the cable to the latch of the vehicle including a connected state or a disconnected state. The state of the latch mechanism can be used to lock the latch to the vehicle or release the latch from the vehicle.

The winch can lower the vehicle into the tank at a predetermined speed or rate. The winch can lower the vehicle into the tank based on the amount of fluid remaining in the tank, or the amount of fluid contained in the tank. Depending on the level of the fluid in the tank, the winch can lower the vehicle at a slower rate. The winch can receive an indication of the fluid level within the tank, or otherwise determine the level of the fluid. For example, the winch can include an input device or processor that receives an indication of the fluid level in the tank, or otherwise determine the fluid level within the tank. The winch can be preconfigured to lower the vehicle into the tank at a predetermined rate or default rate.

For example, a tank or other administrator can determine the distance from a floating roof to the tank floor with reasonable accuracy using a gauge, predetermined construction drawings, or a tape measure (e.g., the cable used to launch and recover the vehicle can include markings every 10 feet, for example). The tank administrator can provide this information to the system.

At step 504, the winch can remove the cable from the tank subsequent to deploying the vehicle. The winch can remove the cable from the tank after the winch has submerged the vehicle into the flammable fluid or lowered the vehicle to the tank floor. The winch can determine to remove the cable from the tank based, or responsive to, an indication. The winch can receive an indication from a sensor that indicates the vehicle has contacted the tank floor, or that the latch has disconnected the cable from the vehicle. The winch can receive an indication from a sensor that the vehicle has become at least partially submerged in the flammable fluid, or otherwise come into contact with the flammable fluid or the tank floor. The winch can remove the cable based on a time interval. For example, the winch can determine to remove or raise the cable from the tank based on expiration of a countdown timer that is set based on a predetermined vehicle deployment process. In another example, the winch can determine to remove the cable based on detecting that a tension in the cable has fallen below a threshold, which can indicate that the vehicle has contacted the tank floor and is being supported by the tank floor instead of the cable.

The sensor of the winch can determine the vehicle was lowered into the flammable fluid based on the difference on the force measured by the sensor. For example, the vehicle may weigh 100 kg. The sensor can detect a 1000 N force as the vehicle is being lowered into the tank, but prior to the vehicle contacting the fluid. The sensor can detect the force based on a tension associated with the cable connecting the vehicle to the winch. When the vehicle comes into contact with the flammable fluid, the sensor can detect a reduction in the force. For example, the sensor can detect a force of 750N when the vehicle comes into contact with the flammable fluid. As the vehicle becomes increasingly submerged in the fluid, the sensor can detect a further reduction in the force until the vehicle is completely submerged in the fluid. However, since the vehicle may have negative buoyancy, the sensor may still detect some non-zero force, although the detected force may be significantly less than the originally detected weight of the vehicle. The sensor can detect a constant force, or substantially constant force (e.g., less than 5% variation) between the vehicle becomes fully submerged in the fluid and just before the vehicle contacts the tank floor. When the vehicle contacts the tank floor, the sensor can detect a further reduction in force. For example, the sensor can detect a near zero force—or a force only due to the weight of the cable—when the vehicle comes into contact with the tank floor because the tank floor can support the weight of the vehicle.

Thus, the winch can determine, based on a difference between forces measured by the sensor, to reel up the cable based on the vehicle at least partially submerged in the flammable fluid or the vehicle reaching the tank floor. The winch can further determine to remove the cable from the tank based on a timer. The timer can be predetermined based on a historical data indicating a time for the vehicle to be lowered into the tank and disconnect the cable from the latch.

At step 506, the vehicle can execute the diagnostic program. The vehicle can obtain the diagnostic program from memory or storage. The vehicle can select a diagnostic program based on a criteria or factor associated with the tank in which the vehicle is lowered. The vehicle can execute the diagnostic program to determine or identify a diagnosis or diagnostic result. The vehicle can use the diagnostic program, or results thereof, to determine whether to initiate a tank inspection process. For example, if the results of the diagnostic program indicate that there are no system errors, or that the conditions associated with performing a successful tank inspection process have been met, the vehicle can begin the tank inspection. The results of the diagnostic program can indicate an operation condition or status of one or more components of the ATIS or vehicle. The diagnostic program can detect the state of the cable, which can indicate the connection of the cable to the vehicle. The operation condition can include exit condition, wait condition, low power state, cooling state, or high performance state.

At step 508, the vehicle can determine to initiate an exit process based on the diagnostic program result. The diagnostic program result can indicate an exit condition based on at least an amount of power available in the battery, the condition of the vehicle or the one or more components of the ATIS (e.g. temperature, performance, etc.), or an absence of indication of uninspected one or more portions of the tank. The vehicle can determine not to initiate the exit process. Instead, the vehicle can determine to initiate the tank inspection process based on the diagnostic program result. The vehicle can determine not to initiate the exit process, but to execute step 520 based on the diagnostic program result responsive to the storing the quality metric as in step 524.

At step 510, the vehicle can determine whether to initiate a tank inspection process based on the diagnostic program result. If the vehicle determines not to initiate the tank inspection process at step 510, the vehicle can proceed to step 512. The vehicle can determine not to initiate the tank inspection process based on the diagnostic program result. The vehicle can disable the propeller to prevent moving the vehicle based on not initiating the tank inspection process, as in step 512. In another implementation, the diagnostic program can be run before the vehicle latch system detaches the vehicle from the cable. By doing so, recovery is facilitated if errors are found during execution of the diagnostic program.

For example, the vehicle can disable the propeller to prevent moving the vehicle. The propeller can be disabled by the control unit using the propeller control program based on the diagnostic program result. The vehicle can then execute the diagnostic program responsive to disabling the propeller. The vehicle can execute the diagnostic program in a manner similar to step 506. The diagnostic program result can indicate at least one operation condition including a waiting condition or a cooling state. The cooling state can be based on the temperature of the vehicle or the one or more components of the ATIS. The waiting condition can be based on the diagnostic program requiring one or more additional results, for example, results from testing the components of the ATIS.

If, however, the vehicle determines to initiate the tank inspection process at step 510, the vehicle can proceed to step 514. At step 514, the vehicle can initiate the tank inspection process by generating and providing one or more commands, such as a command to move the vehicle through the flammable fluid. The vehicle can move through the flammable fluid by a propeller. The vehicle can execute, by the control unit, the diagnostic program prior to causing the propeller to move the vehicle. The vehicle can use the propeller to move to a plurality of portions of the tank. The vehicle can use the ranging device concurrent to traversing the plurality of portions of the tank. The vehicle can configure the propeller to turn in a plurality of directions to move the vehicle in one or more directions.

At step 516, the vehicle can generate a map of the tank. The generation of the tank map 130 can be based on the vehicle traversing the plurality of portions of the tank. The vehicle can further generate a map without traversing the plurality of portions of the tank using the ranging device, such as an infrared sensor, an ultrasonic sensor, electromagnetic radiation sensor (laser) or a radar sensor. The map of the tank can be stored in the tank map within the vehicle resource repository. In some implementations, the control unit 104 of the vehicle can detect an exit condition based on the generated tank map, for example, the vehicle can be provided, based on the available power of the battery corresponding to the size of the tank, with the exit condition by the diagnostic program.

At step 518, the vehicle can determine a first position of the vehicle on the tank map 130. The first position can be determined based on information provided by the ranging device, for example, the ranging device can be configured by the mapping unit 108 to identify or update the position of the vehicle. The first position can indicate the position of the lid with respect to the tank, the lid used for lowering the vehicle into the tank. The first position 302 can be the first uninspected portion of the tank. The vehicle can determine, by the control unit based on one or more results of the diagnostic program, to initiate the tank inspection process. In some implementations, the tank inspection process can command the vehicle to determine a quality metric for the first position. The vehicle can provide an indication of an inspected portion to the tank map or remove an indication of an uninspected portion from the tank map using the ranging device responsive to determining the quality metric for the first position of the tank.

At step 520, the vehicle can cause the propeller to move from the first position to a second position using the control unit. The control unit can provide a command to cause the propeller to move the vehicle from the first position to the second position based on at least the determined first position or the determined quality metric 136 corresponding to the first position based on the tank inspection process. The vehicle can be configured by the control unit, based on the diagnostic program 138, to disable the propeller to prevent the propeller from moving the vehicle from the second position. The second position can correspond to at least one uninspected portion of the tank. The speed of the propeller can be set or adjusted by the control unit based on the result of the diagnostic program 138, the result can be an operation condition, such as, an exit condition, a wait condition, a low power state, a cooling state, or a high performance state, as described in FIG. 1. The speed of the propeller can be set or adjusted based on a current position of the vehicle on the tank map. For example, the control unit can increase the speed of the propeller to move from the first position, decrease the speed of the propeller prior to reaching the second position, and disable the propeller based on the vehicle reaching the second position. The control unit can configure the propeller to move the vehicle in a different direction (e.g. reverse or sideways) based on the vehicle straying from the second position.

At step 522, the vehicle can determine a quality metric for at least one portion of the tank corresponding to the second position on the tank map via the inspection device. The inspection device can include a magnetic sensor, a magnetic sensor array, an ultrasonic array system, an ultrasonic phased array system, or a sweeping device. The sweeping device can include a brush for sweeping one or more substance off at least one portion of the tank. The quality metric can indicate a thickness of the portion of the tank at the second position within the tank. The vehicle can determine, based on the quality metric of the portion of the tank, to determine an additional quality metric for the portion of the tank, the additional quality metric can be determined using at least one different component of the inspection device. For example, the vehicle can determine a quality metric corresponding to the second position using the magnetic sensor of the inspection device, determine the quality of the information from the inspection device, and determine an additional quality metric corresponding to the second position using the ultrasonic array system based on obtaining a low quality information of the quality metric. The quality of the information can be based on a signal-to-noise ratio.

The vehicle can collect data from multiple sensing devices or inspection devices simultaneously (e.g., at the same time or overlapping times or immediately one after the other). The vehicle can record data from both sensors for further processing. The vehicle can perform real-time analysis of the data to determine whether one sensor is faulty, and switch to the other sensor.

At step 524, the vehicle can store the quality metric in the vehicle resource repository. The quality metric can correspond to at least the first position or the second position within the tank. The vehicle resource repository can be a data structure in memory of the vehicle. The vehicle resource repository can be accessed by the control unit. The quality metric corresponding to a position can indicate the one or more inspected portions of the tank. The indication of at least one uninspected portion of the tank can be based on an absence of the quality metric corresponding the portion of the tank, which can be released responsive to storing the quality metric corresponding to the portion of the tank. The vehicle can initiate the diagnostic program responsive to storing the quality metric in the vehicle resource repository. The diagnostic program result can configure the vehicle to initiate the exit process or cause the propeller to move the vehicle to at least one uninspected portion of the tank similar to moving the vehicle from the first position to the second position, as in step 520.

At step 526, the vehicle can initiate the exit process based on an exit condition from the diagnostic program result. The diagnostic program provides the exit condition based on generating the tank map, the power available in the battery, the absence of at least one uninspected portion of the tank, or an expiration of a timer of the tank inspection process, as described in FIG. 1. The exit process can include one or more commands to at least move the vehicle towards the first position of the tank, which can be the position of the lid 204, reel down the cable to the vehicle, cause the latch mechanism to re-engage the cable to couple the cable to the vehicle, or terminate vehicle operation. The termination of vehicle operation can include disabling the components of the vehicle.

Figure 6:
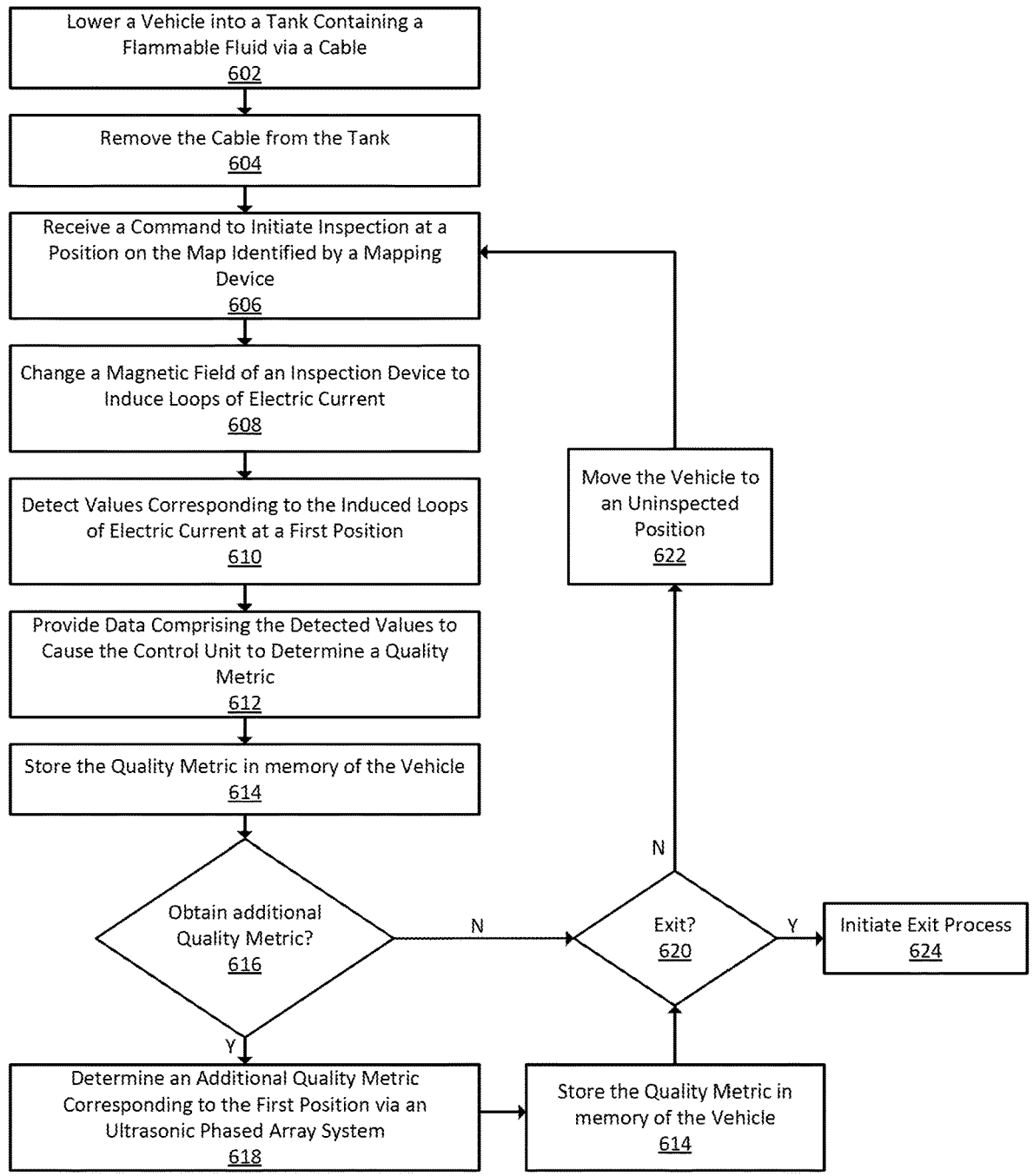
FIG. 6 is a flow diagram of an example method of inspecting a tank containing a flammable fluid.

FIG. 6 is a flow diagram of an example method of inspecting a tank containing a flammable fluid. The method 600 can be performed by system 100, system 400, or one or more component thereof. In brief overview, at step 602, a winch can lower at least one vehicle into a tank containing a flammable fluid via a cable. At step 604, the winch can remove the cable from the tank. At step 606, an inspection device can receive at least one command to initiate an inspection at a position on the map identified by a ranging device. At step 608, the inspection device can change at least one magnetic field to induce loops of electric current. At step 610, the inspection device can detect one or more values corresponding to the induced loops of electric current at a first position. At step 612, the inspection device can provide data comprising the detected values to cause the control unit to determine a quality metric. At step 614, the vehicle can store the quality metric in memory of the vehicle. At step 616, the vehicle can determine to obtain additional quality metric. At step 618, the vehicle can determine an additional quality metric corresponding to the first position via an ultrasonic array or phased-array system. At step 620, the vehicle can determine to initiate an exit process, as in step 624, based on a result of the diagnostic program. At step 622, the control unit can configure the vehicle to move to an uninspected portion of the tank. At step 624, the vehicle can initiate the exit process.

Still referring to FIG. 6, and in further detail, a winch can lower at least one vehicle into a tank containing a flammable fluid via a cable at step 602 similar to step 502 of method 500. At step 604, the winch can remove the cable from the tank subsequent to deploying the vehicle similar to step 504 of method 500. At step 606, an inspection device can receive at least one command from the control unit. The inspection device can receive the command responsive to the ranging device identifying a first position of the vehicle on the tank map. The command can include an instruction to initiate an inspection at the first position on the map. The command can be based on the tank inspection process, which can be configured based on a result of the diagnostic program. The command can include, for example, enabling or disabling the inspection device, moving the inspection device to a different portion of the tank corresponding to the first position, or changing the inspection device type. The inspection device type can change, for example, from one or more magnetic conductors to ultrasonic array or phased array system or vice versa. The ranging device can receive a command, based on the tank inspection process prior to the inspection device receiving the inspection command, to generate the tank map based on a plurality of acoustic waves reflected off one or more portions of the tank. Thus, the vehicle can use one inspection device at a time, alternate between inspection devices, use multiple inspection devices simultaneously, or switch from one inspection device to another based on a condition or an event.

At step 608, the inspection device can change, responsive to the command to initiate inspection, at least one magnetic field in the one or more conductors to induce loops of electric current that extend towards at least one portion of the tank corresponding to the first position on the map. The change of magnetic field can include magnitude, intensity, direction, duration, decay time, or frequency to increase or decrease the magnitude or intensity of electric current based on the inspection process. The inspection device can generate at least one pulsed eddy current for measuring thickness or detecting corrosion. The pulsed eddy currents can contain a continuum of frequencies, which can be used to measure electromagnetic response to various frequencies can using a single step. The magnetic field, created by an electric current from the inspection device, can penetrate through the one or more layers or constructions of the tank and stabilize in the layer of the tank. The electrical current generated by the inspection device can be disabled to cause a drop in the magnetic field, which can result in eddy currents appearing in the layers of the tank floor and decrease in strength over time. The pulsed eddy current probe can be used to monitor the decay in eddy currents, the decay time can determine the thickness of the tank. The electrical current magnitude in a given loop can be proportional to the strength of the magnetic field, the area of the loop, and the rate of change of flux, and inversely proportional to the resistivity of a material.

The inspection device can generate eddy currents by a plurality of conductors arranged in an array. A pulsed eddy current array can refer to a nondestructive testing technology that can provide the ability to drive multiple eddy currents coils, which can be placed side by side in the inspection device. Each individual eddy currents coil in the inspection device sends a strong magnetic field towards the floor below the coil and then abruptly releases that field. Each coil then measures the decay time of the eddy currents associated with the release of the magnetic field. The decay time can be converted into a thickness or corrosion level measurement. The inspection device can electronically drive and read multiple eddy currents sensors positioned side by side in the same inspection device assembly.

At step 610, the inspection device can detect one or more values corresponding to the induced loops of electric current at a first position. The inspection device can re-inspect the first position of the tank based on at least the tank inspection process, or the detected values. The values can be an indication of the distortion, the magnitude or the intensity of the magnetic field or electric current, a rate of decay of the magnetic field, or a duration of the magnetic field decaying to zero. The values can indicate a flaw in the tank, the corrosion of the tank, or the thickness of the tank. The values can be stored in the collected data of the vehicle resource repository, which can determine the quality metric of the tank.

At step 612, the inspection device can provide data comprising the detected values to cause the control unit to determine a quality metric at the portion of the tank corresponding to the first position of the vehicle on the map. The data can be raw information detected by the inspection device, which can be provided to the control unit. The quality metric can determine the thickness or the corrosion level of the tank based on the data. For example, the inspection device can detect the plurality of values using at least one inspection technique (e.g., pulsed eddy current or pulsed eddy current array), the values can be raw information. The inspection device can aggregate the values into a single data packet to provide to the control unit. The control unit can determine the quality metric of the tank based on the values, the quality metric indicating at least the thickness or the corrosion level of the tank. The quality metric can be based on the pulsed eddy current or the pulsed eddy current array corresponding to at least the first position or the second position of the vehicle.

At step 614, the vehicle can store the quality metric in memory of the vehicle (e.g. vehicle resource repository) similar to step 524 of method 500. The stored quality metric can be provided to a remote data repository of a data processing system ("DPS") to store in a historical data via a network. The historical data of the remote data repository of the data processing system can include at least one previously stored quality metric, the quality metric can indicate a predictive corrosion metric based on a plurality of tank inspection performed by the vehicle during a time interval. The model generator can generate a risk-based inspection model based on a time-series of quality metrics determined based on the loops of electric current provided by the inspection device that extend towards the portion of the tank. The model generator 406 can aggregate the historical data obtained from the plurality of tank inspections, and forecast, based on a forecast engine using the historical data, a level of thickness of the tank based on the quality metric, as referred to in FIG. 4.

At step 616, the vehicle can determine, based on the tank inspection process or the result of the diagnostic program, to obtain additional quality metric at the portion of the tank corresponding to the first position of the vehicle on the tank map. The additional quality metric can be obtained using a different inspection device or inspection technique, such as the ultrasonic array or phased array system of the inspection device. For example, the tank inspection process can configure the vehicle to obtain an additional quality metric to average between the quality metric obtained using the magnetic field and the additional quality metric to store as the quality metric for the portion of the tank corresponding to the first position. The diagnostic program result can indicate the quality of the inspection based on the quality metric. For example, the diagnostic program can determine an insufficient quality of the inspection and provide an indication to obtain additional quality metric to the vehicle, based on a signal-to-noise ratio, or the detected values.

At step 618, the vehicle can determine an additional quality metric corresponding to the first position of the vehicle on the tank map via an ultrasonic array system of the inspection device. The additional quality metric can be a second quality metric. The ultrasonic array system can comprise a plurality of ultrasonic transducers, which can be pulsed independently using computer-calculated timing, which can be used to steer the beam to scan the one or more portions of the tank. In some implementations, the inspection device can include two different technologies, and take advantage of their complementarity. For example, eddy current technology will provide better results in the presence of residual sediment after the brush cleans the floor or in case of topside corrosion. Ultrasonic will provide better results when the floor has been sufficiently cleaned by the brush and is primarily affected by pitting. The quality metrics from both technologies can be stored in the memory of the vehicle as in step 614.

At step 620, the vehicle can determine to initiate an exit process based on a result of the diagnostic program similar to step 508. At step 622, the control unit can move vehicle to an uninspected portion of the tank. The vehicle can be moved to the uninspected portion of the tank similar to moving the vehicle from the first position to a second position as in step 520. At step 624, the vehicle can initiate the exit process similar to step 526.

Figure 7:
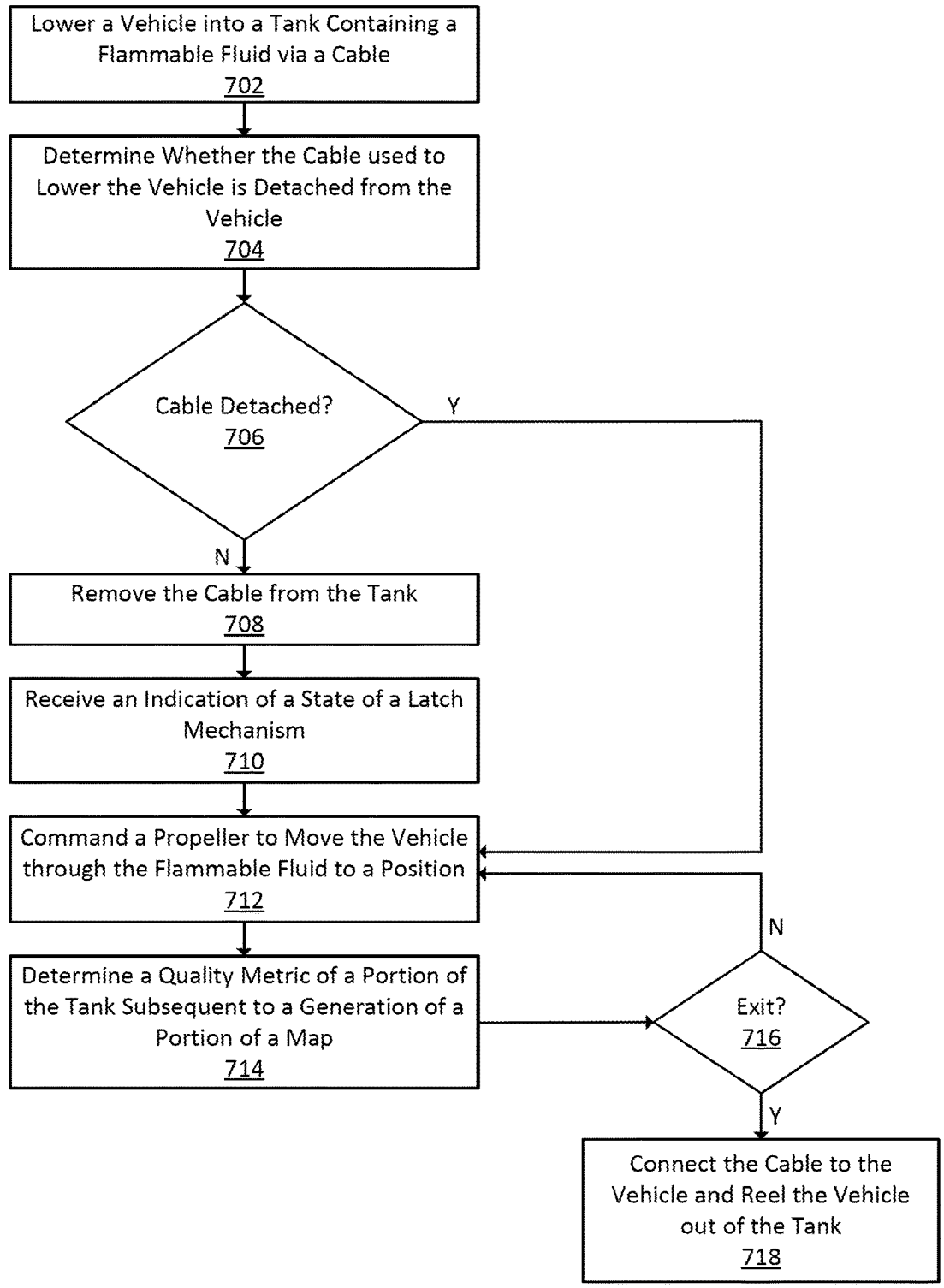
FIG. 7 is a flow diagram of an example method of inspecting a tank containing a flammable fluid.

FIG. 7 is a flow diagram of an example method of inspecting a tank containing a flammable fluid. The method 700 can be performed by system 100, system 400, or one or more component thereof. In brief overview, at step 702, a winch can lower at least one vehicle into a tank containing a flammable fluid via a cable. At step 704, the vehicle can determine whether the cable used to lower the vehicle is detached from the vehicle. At step 706, the vehicle can initiate at least one operation based on the state of the latch mechanism. At step 708, the winch can remove the cable from the tank. At step 710, the vehicle can receive an indication of the state of the latch mechanism. At step 712, the vehicle can command a propeller to move the vehicle through the flammable fluid to a position. At step 714, the vehicle can determine a quality metric of a portion of the tank subsequent to a generation of a portion of a map. At step 716, the vehicle can determine to initiate an exit process. At step 718, the winch can connect the cable to the vehicle using the latch mechanism and reel the vehicle out of the tank based on the exit process.

Still referring to FIG. 7, and in further detail, a winch can lower at least one vehicle into a tank containing a flammable fluid 208 via a cable at step 702 similar to step 502. The cable can be coupled to the vehicle to lower the vehicle into the flammable fluid via the latch mechanism.

At step 704, the vehicle using the control unit can determine, based on a state of the latch mechanism, whether the cable used to lower the vehicle into the tank containing the flammable fluid is detached from the vehicle. The state of the latch mechanism can include a connected state or a disconnected state, which can be detected based on the control unit executing the diagnostic program using at least one sensor. The connected state can indicate a connection between the cable can the latch mechanism. The disconnected state can indicate a disconnection or an absence of connection between the cable and the latch mechanism. The state of the latch mechanism can be based on the flow of current of the latch mechanism detected by the sensor of the vehicle.

At step 706, the vehicle can initiate at least one operation based on the state of the latch mechanism. The operation can include disconnecting the cable from the latch mechanism of the vehicle, which the winch can then remove the cable from the tank, as in step 708, or commanding at least one propeller of the vehicle to move the vehicle through the flammable fluid, as in step 712. The operation can include an exit process, for example, the latch mechanism can indicate the connected state, based on connecting the cable to the latch mechanism of the vehicle, to initiate the exit process. The state of the latch mechanism can determine the result of the diagnostic program.

At step 708, the winch can remove the cable from the tank subsequent to deploying the vehicle similar to step 504. The removal of the cable from the tank can be responsive to disengaging the cable used to lower the vehicle into flammable fluid 208 in the tank via the latch mechanism. The disengagement of the cable can be initiated via unlocking, by the control unit in communication with an actuator of the vehicle, the latch mechanism to disengage the cable subsequent to the vehicle lowered into the flammable fluid in the tank based on a policy and the state of the latch mechanism.

At step 710, the vehicle using the control unit can receive an indication of the state of the latch mechanism. The control unit can execute the diagnostic program responsive to receiving the indication of the state of the latch mechanism. The diagnostic program can provide a result to initiate the tank inspection process based on the disconnected state of the latch mechanism. The control unit can detect the indication of the state via the sensor of the vehicle. The state of the latch mechanism can be the disconnected state based on disconnecting the cable from the latch mechanism. In some cases, the control unit can receive an indication that the cable is decoupled from the vehicle in the flammable fluid 208 from a remote computing device (e.g. data processing system), for example, the remote computing device can provide the indication via a network based on the winch removing the cable from the tank.

At step 712, the vehicle can command a propeller to move the vehicle through the flammable fluid to a position using the control unit responsive to the determination that the cable is detached from the vehicle similar to step 514 or step 520. The command can be generated based on the tank inspection process to control the propeller or the latch mechanism coupling the cable to the vehicle. In some cases, the control unit can receive an indication to perform the tank inspection process comprising causing the propeller to move the vehicle to one or more positions of the tank and determine one or more quality metric from the remote computing device. The remote computing device can be the data processing system 402 in connection with the administrator device. The command can be based on the diagnostic program result indicating the disconnected state of the latch mechanism. For example, a first state can be the connected state and a second state can be the disconnected state. The control unit can command the latch mechanism to decouple the cable from the vehicle in the flammable fluid based on the first state. The sensor 116 of the vehicle can receive an indication of the second state based on disconnecting the cable. The vehicle can then command the propeller to move responsive to the indication of the second state.

At step 714, the control unit of the vehicle can determine a quality metric of a portion of the tank via an inspection device and subsequent to a generation of a portion of a map via a ranging device similar to aggregating step 514, step 516, or step 522. The vehicle can initiate the ranging device concurrent to the inspection device to synchronously update or generate the map of the tank and determine the quality metric of the portion of the tank. The determining of the quality metric and generation of the portion of the map can be based on the tank inspection process. The plurality of portions of the tank can be a plurality of uninspected portions of the tank. For example, the vehicle can reside in a first position of the tank based on the ranging device generating a first portion of the tank map. The vehicle can obtain a first quality metric of the first portion of the tank corresponding to the first position using the inspection device subsequent to the generation of the first portion of the tank map. The vehicle can move to a second position different than the first position. The ranging device can generate a second portion of the tank map and subsequently inspect the second portion corresponding to the second position using the inspection device. The vehicle can traverse the plurality of portions of the tank based on an indication of an uninspected portion of the tank.

At step 716, the vehicle can determine to initiate an exit process similar to step 508. At step 718, the winch can connect the cable to the vehicle using the latch mechanism and reel the vehicle out of the tank based on the exit process similar to step 526. The control unit in communication with the actuator of the vehicle can lock the latch mechanism to engage the cable to the vehicle. For example, the control unit can detect an exit condition in the tank inspection process. The control unit can command the propeller to move the vehicle to a position under the lid 204 of the tank. The cable can be reeled down to the vehicle by the winch. The vehicle can then re-engage the latch mechanism with the cable to couple the cable to the vehicle. The winch can reel up the vehicle responsive to detecting that the cable is coupled to the vehicle.

Figure 8:
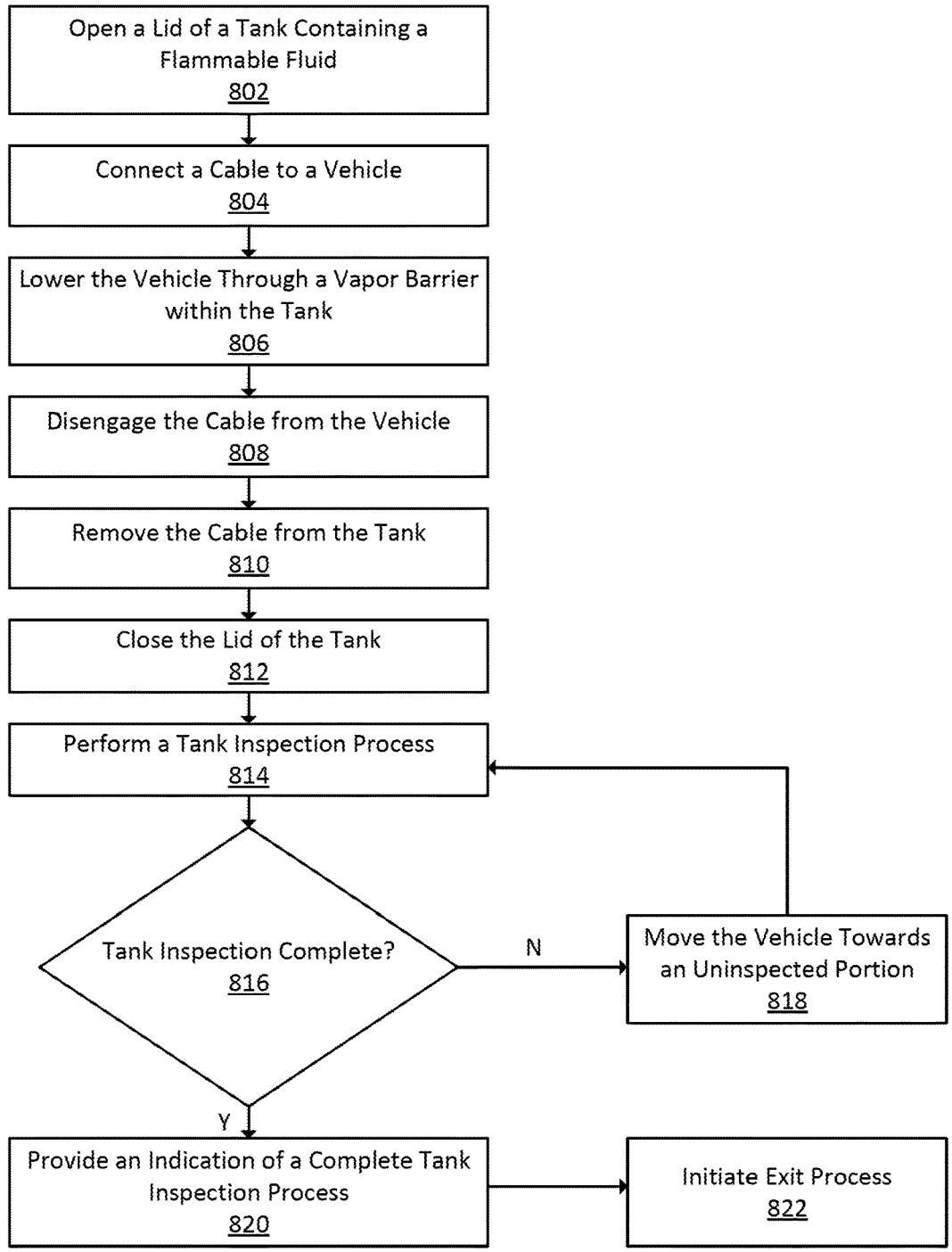
FIG. 8 is a flow diagram of an example method of inspecting a tank containing a flammable fluid.

FIG. 8 is a flow diagram of an example method of inspecting a tank containing a flammable fluid. The method 800 can be performed by system 100, system 400, or one or more component thereof. In brief overview, at step 802, a lid of a tank containing a flammable fluid can be opened. At step 804, a winch can connect a cable to a vehicle. At step 806, the winch can lower the vehicle through a vapor layer within the tank via a cable. At step 808, the latch mechanism can disengage the cable from the vehicle. At step 810, the winch can remove the cable from the tank. At step 812, the lid of the tank can be closed. At step 814, the vehicle can perform a tank inspection process. At step 816, the vehicle can determine whether the tank inspection process is complete based on a diagnostic program result. At step 818, the vehicle can move towards an uninspected portion of the tank based on an incomplete tank inspection process. At step 820, the diagnostic program result can provide an indication of a complete tank inspection process. At step 822, the vehicle can initiate an exit process.

Still referring to FIG. 8, and in further detail, a lid of a tank containing a flammable fluid can be opened at step 802. The lid can be opened manually using various lid opening tools. At step 804, a winch can connect the cable to the vehicle. The cable can be connected to the latch mechanism of the vehicle. The winch can be external to the tank. The latch mechanism can include an actuator to lock or unlock the cable from the vehicle. The latch mechanism can indicate a state based on the connection of the cable to the vehicle.

At step 806, the winch can lower the vehicle through a vapor layer 206 within the tank and on top of the flammable fluid via a cable and through an opening of the tank similar to step 502. The winch can unreel the cable connected to the vehicle to lower the vehicle into the tank.

At step 808, the latch mechanism can disengage the cable from the vehicle similar to step 504 or step 708. The disengagement of the cable can be initiated via unlocking, by the control unit in communication with an actuator of the vehicle, the latch mechanism to disengage the cable subsequent to the vehicle lowered into the flammable fluid in the tank based on at least one policy and the state of the latch mechanism. The latch mechanism can determine whether the cable was detached based on a sensor, such as a mechanical sensor, on the cable indicating a disconnection from the latch of the vehicle or on the winch indicating the vehicle was lowered into the flammable fluid.

At step 810, the winch can remove the cable from the tank by reeling the cable subsequent to disengaging the cable from the vehicle similar to step 504. At step 812, the lid 204 of the tank can be closed to seal the vehicle inside the tank responsive to removing the cable from the tank. The closing of the lid can be similar to opening the lid, as in step 802.

At step 814, the vehicle can be configured by the control unit to perform a tank inspection process under battery power based on the cable disconnected from the vehicle similar to step 606. The tank inspection process can include generating a map of the tank and determining a quality metric for a portion of the tank corresponding to a location on the generated tank map. The vehicle can initialize a map data structure (e.g. tank map) for the tank in memory (e.g. vehicle resource repository) of the vehicle. The vehicle can store the tank map in the map data structure. The control unit of the vehicle can determine, upon being lowered into the tank, to generate the tank map and instruct the ranging device to generate the map of the tank. The vehicle can be configured with a predetermined duration to perform the tank inspection process, the predetermined duration can be stored in a configuration file or collected data in memory of the vehicle. The vehicle can initiate a timer based on the predetermined duration responsive to being sealed in the tank and beginning the tank inspection process.

At step 816, the vehicle can determine whether the tank inspection process is complete based on a diagnostic program result. The control unit can identify an uninspected portion of the tank based on the generated tank map, which can be provided in the diagnostic program result. The diagnostic program result can cause the vehicle to move the vehicle towards the uninspected portion, as in step 818, or initiate an exit process based on an indication of complete tank inspection process, as in 822. The diagnostic program result can provide the vehicle with an indication of complete tank inspection process based on an absence of any uninspected portions of the floor of the tank based on the generated tank map.

At step 818, the vehicle can move towards an uninspected portion of the tank based on an incomplete tank inspection process similar to step 622. At step 820, the diagnostic program result can provide an indication of a complete tank inspection process. The indication of the complete tank inspection process can be based on an absence of any uninspected portions of the floor of the tank based on the generated tank map. The indication of the complete tank inspection process can include a wireless signal or acoustic signal. The wireless signal can be sent to a data processing system ("DPS") connected an administrator device via a network. The acoustic signal can be transmitted by the vehicle via a speaker of the vehicle. The indication of the complete tank inspection process can initiate the exit process, as in step 822.

At step 822, the vehicle can initiate an exit process similar to step 526 or step 718. In some cases, the vehicle can initiate the exit process to terminate the tank inspection process responsive to an expiration of the timer. The time of expiration can be predetermined or configured via the control unit of the vehicle.

Figure 9:
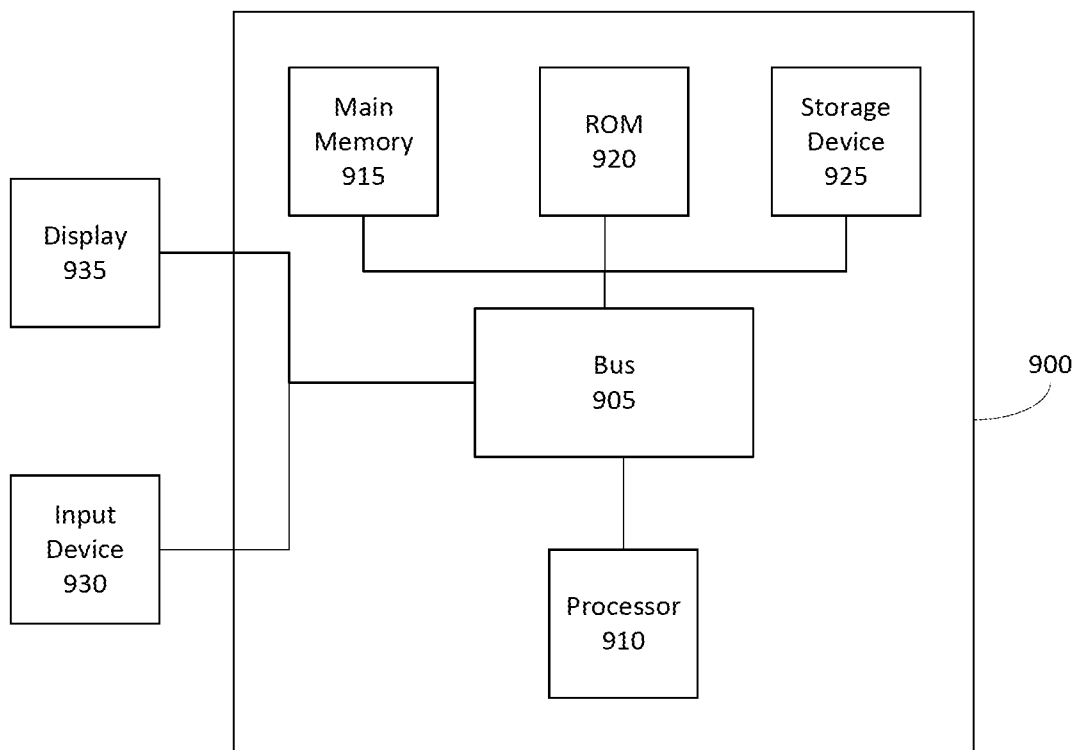
FIG. 9 is a block diagram illustrating an architecture for a computer system that can be employed to implement elements of the systems, methods and apparatus described and illustrated herein, including, for example, the systems and apparatus depicted in FIGS. 1-4, and the methods depicted in FIGS. 5-8.

FIG. 9 is a block diagram of an example computer system 900. The computer system or computing device 900 can include or be used to implement one or more component of system 100, 200, 300, or 400, or perform one or more aspect of the method 500, 600, 700 or 800. For example, the system 900 can implement one or more component or functionality of the ATIS 102, the data processing system 402, the vehicle, or the administrator device 422. The computing system 900 includes at least one bus 905 or other communication component for communicating information and at least one processor 910 or processing circuit coupled to the bus 905 for processing information. The computing system 900 can also include one or more processors 910 or processing circuits coupled to the bus for processing information. The computing system 900 also includes at least one main memory 915, such as a random access memory (RAM) or other dynamic storage device, coupled to the bus 905 for storing information, and instructions to be executed by the processor 910. The main memory 915. The main memory 915 can also be used for storing one or more of a propeller control program, tank map, collected data, tank inspection process, quality metric, diagnostic program, or other information. The computing system 900 may include at least one read only memory (ROM) 920 or other static storage device coupled to the bus 905 for storing static information and instructions for the processor 910. A storage device 925, such as a solid state device, magnetic disk or optical disk, can be coupled to the bus 905 to persistently store information and instructions. The storage device 925 can include or be part of the data repository 126.

The computing system 900 may be coupled via the bus 905 to a display 935, such as a liquid crystal display, or active matrix display, for displaying information to a user of the administrator device 422. An input device 930, such as a keyboard or voice interface may be coupled to the bus 905 for communicating information and commands to the processor 910. The input device 930 can include a touch screen display 935. The input device 930 can also include a cursor control, such as a mouse, a trackball, or cursor direction keys, for communicating direction information and command selections to the processor 910 and for controlling cursor movement on the display 935. The display 935 (e.g., on a vehicle dashboard) can, for example, be part of the ATIS 102, vehicle, data processing system 402, administrator device 422, or other component depicted herein.

The processes, systems and methods described herein can be implemented by the computing system 900 in response to the processor 910 executing an arrangement of instructions contained in main memory 915. Such instructions can be read into main memory 915 from another computer-readable medium, such as the storage device 925. Execution of the arrangement of instructions contained in main memory 915 causes the computing system 900 to perform the illustrative processes described herein. One or more processors in a multi-processing arrangement may also be employed to execute the instructions contained in main memory 915. Hard-wired circuitry can be used in place of or in combination with software instructions together with the systems and methods described herein. Systems and methods described herein are not limited to any specific combination of hardware circuitry and software.

Although an example computing system has been described in FIG. 9, the subject matter including the operations described in this specification can be implemented in other types of digital electronic circuitry, or in computer software, firmware, or hardware, including the structures disclosed in this specification and their structural equivalents, or in combinations of one or more of them.

Some of the description herein emphasizes the structural independence of the aspects of the system components, such as components of the control unit 104, which illustrates one grouping of operations and responsibilities of these system components. Other groupings that execute similar overall operations are understood to be within the scope of the present application. Modules can be implemented in hardware or as computer instructions on a non-transient computer readable storage medium, and modules can be distributed across various hardware or computer based components.

The systems described above can provide multiple ones of any or each of those components and these components can be provided on either a standalone system or on multiple instantiation in a distributed system. In addition, the systems and methods described above can be provided as one or more computer-readable programs or executable instructions embodied on or in one or more articles of manufacture. The article of manufacture can be cloud storage, a hard disk, a CD-ROM, a flash memory card, a PROM, a RAM, a ROM, or a magnetic tape. In general, the computer-readable programs can be implemented in any programming language, such as LISP, PERL, C, C++, C#, PROLOG, or in any byte code language such as JAVA. The software programs or executable instructions can be stored on or in one or more articles of manufacture as object code.

Example and non-limiting module implementation elements include sensors providing any value determined herein, sensors providing any value that is a precursor to a value determined herein, datalink or network hardware including communication chips, oscillating crystals, communication links, cables, twisted pair wiring, coaxial wiring, shielded wiring, transmitters, receivers, or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), or digital control elements.

The subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatuses. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices include cloud storage). The operations described in this specification can be implemented as operations performed by a data processing apparatus on data stored on one or more computer-readable storage devices or received from other sources.

The terms "computing device", "component" or "data processing apparatus" or the like encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, app, script, or code) can be written in any form of programming language, including compiled or interpreted languages, declarative or procedural languages, and can be deployed in any form, including as a stand-alone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data can include non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The subject matter described herein can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or a combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

The systems and methods described herein may be embodied in other specific forms without departing from the characteristics thereof. Scope of the systems and methods described herein is thus indicated by the appended claims, rather than the foregoing description, and changes that come within the meaning and range of equivalency of the claims are embraced therein.

What is claimed is:

1. A system to inspect a tank containing a flammable fluid, comprising:
    a vehicle comprising a battery, a pressure switch, a control unit, a propeller, an inspection device having one or more conductors, and a ranging device;
    the pressure switch closing an electronic circuit between the control unit and the battery responsive to the pressure switch detecting an ambient pressure greater than a minimum threshold;
    the battery of the vehicle providing, responsive to closing of the electronic circuit by the pressure switch, power to the control unit, the propeller, the inspection device, and the ranging device;
    the control unit generating, based on data received from the ranging device, a map of the tank, and determining a first position of the vehicle on the map of the tank;
    the inspection device receiving, from the control unit responsive to identifying the first position of the vehicle on the map of the tank based on data from the ranging device, a command to initiate inspection at the first position on the map;
    the inspection device changing, responsive to the command to initiate inspection, a magnetic field in the one or more conductors to induce loops of electric current that extend towards a portion of the tank corresponding to the first position on the map;
    the inspection device detecting values corresponding to the induced loops of electric current at the portion of the tank corresponding to the first position on the map;
    the inspection device providing, to the control unit, data comprising the detected values;
    the control unit determining a quality metric at the portion of the tank corresponding to the first position of the vehicle on the map, and storing, in a memory of the vehicle, the quality metric; and
    the propeller of the vehicle moving, responsive to a second command from the control unit, the vehicle through the flammable fluid in the tank towards a second position on the map.

2. The system of claim 1, comprising:
a latch mechanism of the vehicle configured to couple the vehicle to a passive metal rope used to lower the vehicle into the flammable fluid in the tank;
a sensor of the vehicle configured to determine that the vehicle is in contact with the floor of the tank; and
the latch mechanism decoupling the passive metal rope from the vehicle responsive to the sensor indicating that the vehicle is in contact with the floor of the tank.

3. The system of claim 1, wherein the control unit is further configured to:
determine, based on results of a diagnostic program, to initiate a tank inspection process; and
provide, based on the tank inspection process, the second command to cause the propeller to move the vehicle from the first position to the second position within the tank.

4. The system of claim 1, wherein the ranging device detects acoustic waves reflected off one or more portions of the tank, and the control unit generates the map of the tank based on the detected acoustic waves.

5. The system of claim 1, wherein the inspection device comprises an ultrasonic phased array system.

6. The system of claim 1, wherein the inspection device comprises at least two different types of sensors, and selects, based on a condition associated with the portion of the tank corresponding to the first position of the vehicle on the map, one of the at least two different types of sensors to inspect the portion of the tank.

7. The system of claim 1, wherein the inspection device comprises at least two different types of sensors, and is configured to:
select, based on a condition associated with the portion of the tank corresponding to the first position of the vehicle on the map, one of the at least two different types of sensors to inspect the portion of the tank; and
select, based on a condition associated with a portion of the tank corresponding to the second position of the vehicle on the map, the other of the at least two different types of sensors to inspect the portion of the tank corresponding to the second position.

8. The system of claim 1, wherein the quality metric indicates a predictive corrosion metric based on a plurality of tank inspections performed by the vehicle during a time interval.

9. The system of claim 1, wherein the control unit is configured to:
identify an uninspected portion of the tank based on the map; and
cause the propeller of the vehicle to move the vehicle towards the identified uninspected portion of the tank.

10. The system of claim 1, wherein the control unit is configured to:
identify an absence of any uninspected portions of a floor of the tank based on the map; and
provide, responsive to identification of the absence, an indication that a tank inspection process is complete.

11. A method of inspecting a tank containing a flammable fluid, comprising:
providing a vehicle comprising a battery, a pressure switch, a control unit, a propeller, an inspection device having one or more conductors, and a ranging device;
closing, by the pressure switch, an electronic circuit between the control unit and the battery responsive to the pressure switch detecting an ambient pressure greater than a minimum threshold;
providing, by the battery of the vehicle responsive to closing of the electronic circuit by the pressure switch, power to the control unit, the propeller, the inspection device, and the ranging device;
generating, by the control unit based on data received from the ranging device, a map of the tank, and determining a first position of the vehicle on the map of the tank;
receiving, by the inspection device from the control unit responsive to identifying the first position of the vehicle on the map of the tank based on data from the ranging device, a command to initiate inspection at the first position on the map;
changing, by the inspection device responsive to the command to initiate inspection, a magnetic field in the one or more conductors to induce loops of electric current that extend towards a portion of the tank corresponding to the first position on the map;
detecting, by the inspection device, values corresponding to the induced loops of electric current at the portion of the tank corresponding to the first position on the map;
providing, by the inspection device to the control unit, data comprising the detected values;
determining, by the control unit, a quality metric at the portion of the tank corresponding to the first position of the vehicle on the map, and storing, in a memory of the vehicle, the quality metric; and
moving, by the propeller of the vehicle responsive to a second command from the control unit, the vehicle through the flammable fluid in the tank towards a second position on the map.

12. The method of claim 11, comprising:
coupling, via a latch mechanism of the vehicle, the vehicle to a passive metal rope used to lower the vehicle into the flammable fluid in the tank;
determining, by a sensor of the vehicle, that the vehicle is in contact with the floor of the tank; and
decoupling, via the latch mechanism, the passive metal rope from the vehicle responsive to the sensor indicating that the vehicle is in contact with the floor of the tank.

13. The method of claim 11, comprising:
determining, by the control unit based on results of a diagnostic program, to initiate a tank inspection process; and
providing, by the control unit based on the tank inspection process, the second command to cause the propeller to move the vehicle from the first position to the second position within the tank.

14. The method of claim 11, comprising:
detecting, by the ranging device, acoustic waves reflected off one or more portions of the tank; and
generating, by the control unit, the map of the tank based on the detected acoustic waves.

15. The method of claim 11, wherein the inspection device comprises an ultrasonic phased array system.

16. The method of claim 11, wherein the inspection device comprises at least two different types of sensors, comprising:
selecting, based on a condition associated with the portion of the tank corresponding to the first position of the vehicle on the map, one of the at least two different types of sensors to inspect the portion of the tank.

17. The method of claim 11, wherein the inspection device comprises at least two different types of sensors, comprising:
selecting, based on a condition associated with the portion of the tank corresponding to the first position of the vehicle on the map, one of the at least two different types of sensors to inspect the portion of the tank; and selecting, based on a condition associated with a portion of the tank corresponding to the second position of the vehicle on the map, the other of the at least two different types of sensors to inspect the portion of the tank corresponding to the second position.

18. The method of claim 11, wherein the quality metric indicates a predictive corrosion metric based on a plurality of tank inspections performed by the vehicle during a time interval.

19. The method of claim 11, comprising:
identifying, by the control unit, an uninspected portion of the tank based on the map; and
moving, by propeller, the vehicle towards the identified uninspected portion of the tank.

20. The method of claim 11, comprising:
identifying, by the control unit, an absence of any uninspected portions of a floor of the tank based on the map; and
providing, by the control unit responsive to identification of the absence, an indication that a tank inspection process is complete.

* * * * *